(12) United States Patent
Tsuji et al.

(10) Patent No.: US 10,508,295 B2
(45) Date of Patent: Dec. 17, 2019

(54) GAMMA GLUTAMYL-VALINE SYNTHASE, AND METHOD FOR PRODUCING GAMMA GLUTAMYL-VALYL-GLYCINE

(71) Applicant: AJINOMOTO CO., INC., Tokyo (JP)

(72) Inventors: Chihiro Tsuji, Kawasaki (JP); Hiroyuki Nozaki, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 15/234,119

(22) Filed: Aug. 11, 2016

(65) Prior Publication Data

US 2016/0340707 A1 Nov. 24, 2016

Related U.S. Application Data

(63) Continuation of application No. PCT/JP2015/056425, filed on Mar. 4, 2015.

(30) Foreign Application Priority Data

Mar. 5, 2014 (JP) .................. 2014-042584

(51) Int. Cl.
| | | |
|---|---|---|
| C12P 21/02 | (2006.01) | |
| C12N 9/00 | (2006.01) | |
| C07K 5/02 | (2006.01) | |
| C12N 15/70 | (2006.01) | |

(52) U.S. Cl.
CPC ............ *C12P 21/02* (2013.01); *C07K 5/0215* (2013.01); *C12N 9/93* (2013.01); *C12N 15/70* (2013.01); *C12Y 603/02002* (2013.01)

(58) Field of Classification Search
None
See application file for complete search history.

(56) References Cited

U.S. PATENT DOCUMENTS

| | | |
|---|---|---|
| 2009/0239310 A1 | 9/2009 | Ohsu et al. |
| 2009/0239808 A1 | 9/2009 | Ohsu et al. |
| 2010/0105864 A1 | 4/2010 | Yoneda et al. |
| 2010/0120698 A1 | 5/2010 | Nagasaki et al. |
| 2010/0183792 A1 | 7/2010 | Nagasaki et al. |
| 2010/0203592 A1* | 8/2010 | Tabata ............... C07K 14/195 435/71.2 |
| 2011/0046046 A1 | 2/2011 | Hara et al. |
| 2011/0071075 A1 | 3/2011 | Takeuchi et al. |
| 2014/0212920 A1 | 7/2014 | Nozaki et al. |
| 2015/0361133 A1 | 12/2015 | Iwasaki |
| 2016/0326510 A1 | 11/2016 | Sasahara et al. |

FOREIGN PATENT DOCUMENTS

| | | | |
|---|---|---|---|
| EP | 3 101 130 A1 | 12/2016 | |
| JP | 08-119916 A | 5/1996 | |
| JP | 2012-085637 A | 5/2012 | |
| WO | WO 2013/054447 A1 | 4/2013 | |
| WO | WO-2013178808 A2 * | 12/2013 | .......... C12N 9/16 |

OTHER PUBLICATIONS

Machine-language translation of WO 2013/054447 A1, retrieved from www.wipo.int/patentscope/en/ on Jan. 22, 2018, 16 pages.*
White et al., Analyt. Biochem. 318:175-180, 2003.*
International Search Report dated Jun. 2, 2015, in PCT/JP2015/056425 (filed Mar. 4, 2015).
putative glutamate—cysteine ligase [Kocuria rhizophila DC2201]. (online), May 8, 2009 (retrieved on May 18, 2015), retrieved from NCBI http://www.ncbi.nlm.nih.gov/protein/163580545?sat=3&satkey=20934206 (entire text).
RecName: Full=Carboxylate-amine ligase Mlut_16620. (online), Feb. 19, 2014 retrieved May 18, 2015) retrieved from NCBI http://www.ncbi.nlm.nih.gov/protein/259585572?sat=18&satkey=5410714 (entire text).
RecName: Full=Carboxylate-amine ligase cgR_2639. (online), Feb. 19, 2014 (retrieved on May 18, 2015) retrieved from NCBI http://www.ncbi.nlm.nih.gov/protein/166991419?sat=18&satkey=5452487 (entire text).
Kelly, Brenda S., et al., "*Escherichia coli* γ-Glutamylcysteine Synthetase Two Active Site Metal Ions Affect Substrate and Inhibitor Binding", The Journal of Biological Chemistry, 2002, vol. 277, No. 1, pp. 50-58.
Kino, Kuniki, et al., "Novel substrate specificity of glutathione synthesis enzymes from *Streptococcus* agalactiae and Clostridium acetobutylicum", Biochemical and Biophysical Research Communications, 2007, 352, pp. 351-359.
Kumagai, Hidehiko, et al., "γ-Glutamylcysteine Synthetase from Proteus mirabilis", Agric. Biol. Chem., 1982, vol. 46, No. 5, pp. 1301-1309.
Vitali, Ronald A., et al., "The Isolation of γ-L-Glutamyl Peptides from a Fermentation Broth", The Journal of Biological Chemistry, 1965, vol. 240, No. 6, pp. 2508-2511.
Partial Supplementary European Search Report dated Oct. 10, 2017 in Patent Application No. 15758161.2.
H. Takarada, et al., "Carboxylate-amine Ligase KRH_06690", Kocuria rhizophila, XP002774013, Database Accession No. B2GJI7, 2014,1 page.
M. Young, et al., "Carboxylate-amine Ligase Mlut_16620", Micrococcus Luteus, XP002774014, Database Accession No. C5CC09, 2014, 1 page.
H. Yukawa, et al., "Carboxylate-amine Ligase CgR_2639", Corynebacterium glutamicum, XP002774015, Database Accession No. A4QHD8, 2014, 1 page.
"Hypothetical protein, partial", Kocuria sp. UCD-OTCP, Database Accession No. WP_017833351, XP002774016, 2013, 1 Page.
G.S. Reddy, et al., "Carboxylate-amine Ligase", Kocuria polaris, XP002774017, Database Accession No. A0A0A6VST0, 2015, 1 page.

* cited by examiner

*Primary Examiner* — David Steadman
(74) *Attorney, Agent, or Firm* — Oblon, McClelland, Maier & Neusdadt, L.L.P.

(57) ABSTRACT

γ-Glu-Val synthetase suitable for generating γ-Glu-Val, and a method for producing γ-Glu-Val-Gly using the same are provided. By using γ-Glu-Val synthetase showing a ratio of γ-glutamylvaline synthetase activity to γ-glutamylglycine synthetase activity of 2.0 or higher, such as γ-Glu-Val synthetase of *Kocuria rosea* (AJ3132), γ-Glu-Val-Gly is produced from Glu, Val, and Gly as raw materials.

19 Claims, 1 Drawing Sheet
Specification includes a Sequence Listing.

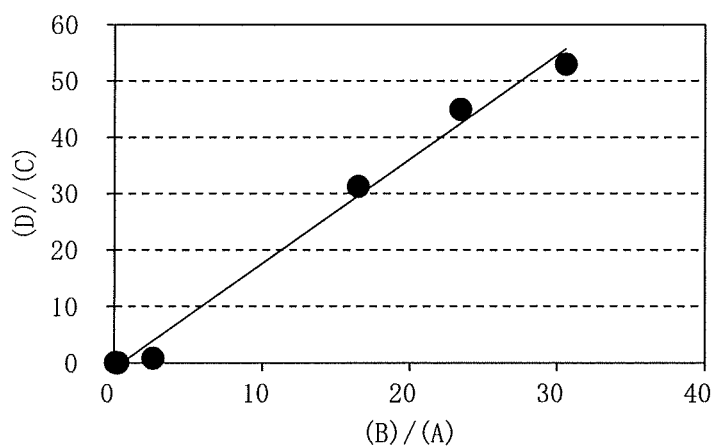

SEQUENCE LISTING

```
<160> NUMBER OF SEQ ID NOS: 30

<210> SEQ ID NO 1
<211> LENGTH: 10
<212> TYPE: PRT
<213> ORGANISM: Kocuria rosea

<400> SEQUENCE: 1

Met Glu Ile Ser Phe Ala Arg Ser His Gln
1               5                   10

<210> SEQ ID NO 2
<211> LENGTH: 13
<212> TYPE: PRT
<213> ORGANISM: Kocuria rosea

<400> SEQUENCE: 2

Val Thr Asp Pro Gln Gly Leu Glu Val Phe Ala Gly Thr
1               5                   10

<210> SEQ ID NO 3
<211> LENGTH: 1146
<212> TYPE: DNA
<213> ORGANISM: Kocuria rosea
```

<400> SEQUENCE: 3

```
gtggagatct cgttcgcccg ctcccaccag tcgacgctgg gcgtcgagtg ggagatcgcc      60
ctcgtggacg gcaccaccgg ggatctcgtc ccccggggcc gggagacgtt cgaggccgtc     120
ctggacgccc accccgcctg gggcacggac ggcgaccacc cgcacctgac cggggagttc     180
ctgctcaaca ccgtcgagct ggtcaccggg gtgtgccggg acgtcgccca ctccaccgag     240
cagctgtcca ccatgctgga cgagatccgc aaggtcaccg accgcaggg cctcgaggtc      300
ttcgccgccg gcacccaccc gttcgcccgc tggcaggacc agcaggtcac cgacaagcag     360
cgctaccaca gctcgtggga ccgcacccag tactgggggcc ggcagatggt catctacggg    420
gtgcacgtgc acgtgggcct cgactcccgg gcgaaggcgc tgcccgtgct ggacgggctg     480
ctgacctact acccgcacct gctggcgctg tccgcgaact cgcccttctg ggcggggcgag    540
gacaccggct atgcgtccca gcgctccatg atcttccagc agctgtccac ggcggggctg     600
ccgtaccact ccccgtcctg ggacgcgtac gagcagtgca tcacggacat gatcgccacc     660
ggcatcatcg aggagatgag cgaggcccgc tgggacgtgc gccccgtgcc ccggctgggc     720
accgacgagg tgcgcttctg cgacgggctc tcgaccctgt gggaggtcgg ggcgctcacg     780
gcgctcaccc agtgcctcgc ggagtccatc tcccgggacg tggaggcggg ccggccccc     840
gcccgcctga gccctggca catccaggag aacaagtggc gcgccgcccg ctacggcctc      900
gacgccgagg tcatcaccga cccgcgcaac gtcgagcggg acctgcgcac ggacctgacc     960
gcgctgctcg accggctgga gcccgtggcc gcgcagctgg gctgctcccg cgagctcgcc    1020
gacgtggagc ggatcctgga gcagggcgcc ggctaccagc gccagcgcgc ggtcgcccgg    1080
gcccacgacg gggacctgca cgccgtcgcc ctcgacatcg tccgccgcac ccgggagaac    1140
gactga                                                               1146
```

<210> SEQ ID NO 4
<211> LENGTH: 31
<212> TYPE: DNA
<213> ORGANISM: Artificial Sequence
<220> FEATURE:
<223> OTHER INFORMATION: primer

<400> SEQUENCE: 4

```
aaacatatgg agatctcgtt cgcccgctcc c                                    31
```

<210> SEQ ID NO 5
<211> LENGTH: 33
<212> TYPE: DNA
<213> ORGANISM: Artificial Sequence
<220> FEATURE:
<223> OTHER INFORMATION: primer

<400> SEQUENCE: 5

```
tttaagcttt cagtcgttct cccgggtgcg gcg                                  33
```

<210> SEQ ID NO 6
<211> LENGTH: 381
<212> TYPE: PRT
<213> ORGANISM: Kocuria rosea

<400> SEQUENCE: 6

```
Met Glu Ile Ser Phe Ala Arg Ser His Gln Ser Thr Leu Gly Val Glu
1               5                   10                  15

Trp Glu Ile Ala Leu Val Asp Gly Thr Thr Gly Asp Leu Val Pro Arg
```

```
            20                  25                  30
Gly Arg Glu Thr Phe Glu Ala Val Leu Asp Ala His Pro Ala Trp Gly
            35                  40                  45

Thr Asp Gly Asp His Pro His Leu Thr Gly Glu Phe Leu Leu Asn Thr
    50                  55                  60

Val Glu Leu Val Thr Gly Val Cys Arg Asp Val Ala His Ser Thr Glu
 65                  70                  75                  80

Gln Leu Ser Thr Met Leu Asp Glu Ile Arg Lys Val Thr Asp Pro Gln
                85                  90                  95

Gly Leu Glu Val Phe Ala Ala Gly Thr His Pro Phe Ala Arg Trp Gln
            100                 105                 110

Asp Gln Gln Val Thr Asp Lys Gln Arg Tyr His Lys Leu Val Asp Arg
            115                 120                 125

Thr Gln Tyr Trp Gly Arg Gln Met Val Ile Tyr Gly Val His Val His
        130                 135                 140

Val Gly Leu Asp Ser Arg Ala Lys Ala Leu Pro Val Leu Asp Gly Leu
145                 150                 155                 160

Leu Thr Tyr Tyr Pro His Leu Leu Ala Leu Ser Ala Asn Ser Pro Phe
                165                 170                 175

Trp Ala Gly Glu Asp Thr Gly Tyr Ala Ser Gln Arg Ser Met Ile Phe
            180                 185                 190

Gln Gln Leu Ser Thr Ala Gly Leu Pro Tyr His Phe Pro Ser Trp Asp
        195                 200                 205

Ala Tyr Glu Gln Cys Ile Thr Asp Met Ile Ala Thr Gly Ile Ile Glu
    210                 215                 220

Glu Met Ser Glu Ala Arg Trp Asp Val Arg Pro Val Pro Arg Leu Gly
225                 230                 235                 240

Thr Asp Glu Val Arg Phe Cys Asp Gly Leu Ser Thr Leu Trp Glu Val
                245                 250                 255

Gly Ala Leu Thr Ala Leu Thr Gln Cys Leu Ala Glu Ser Ile Ser Arg
            260                 265                 270

Asp Val Glu Ala Gly Arg Pro Pro Ala Arg Leu Lys Pro Trp His Ile
        275                 280                 285

Gln Glu Asn Lys Trp Arg Ala Ala Arg Tyr Gly Leu Asp Ala Glu Val
    290                 295                 300

Ile Thr Asp Pro Arg Asn Val Glu Arg Asp Leu Arg Thr Asp Leu Thr
305                 310                 315                 320

Ala Leu Leu Asp Arg Leu Glu Pro Val Ala Ala Gln Leu Gly Cys Ser
                325                 330                 335

Arg Glu Leu Ala Asp Val Glu Arg Ile Leu Glu Gln Gly Ala Gly Tyr
            340                 345                 350

Gln Arg Gln Arg Ala Val Ala Arg Ala His Asp Gly Asp Leu His Ala
        355                 360                 365

Val Ala Leu Asp Ile Val Arg Arg Thr Arg Glu Asn Asp
370                 375                 380

<210> SEQ ID NO 7
<211> LENGTH: 1181
<212> TYPE: DNA
<213> ORGANISM: Kocuria rhizophila

<400> SEQUENCE: 7
atgccgttcc cggcgcaccc acgagaggac cacgccgtgc acattgattt cgagacctcc      60
gagaactcca ccctgggtgt ggaatgggag gtcgcgctcg tggaccgcga atccggtgag     120
```

```
ctcgccccgc gcgcccagga ggtcctggag gccgtggtgg gcgagtaccc cgagctcggg      180
gaggagggcg accaccccgca ggtcacgggc gagttcctgc agaacaccgt ggaaatggtc     240
acgggcgtgt gcagcgccgt tcccgaggcg gtggagcacc tcgcgcagac ccaggaccgg     300
atccggaaga tcaccgaccc ccgctccctg gaaatcttcg ccgcgggcac ccacccgttc     360
tcggactgga ccgagcagcc cgtggtggac gcggagcgct actacaaggt cctggaccgg     420
gcgcagtact ggggccggca gatggtgatc ttcggcatgc acgtgcacgt gggcatcgac     480
caccgggaca aggcgctgcc cgtgctcgac gggctcatga actactaccc ccacctgctg     540
gcgctgtccg cgaactcccc ctactggtgc ggccacgaca ccggctacgc ctcccaccgg     600
gcgctgatct tccagcagct ctccaccgcg gggctgccct tccacttcga ctcctggagc     660
gagtacgagg cctacgtctc ggacctcatg gagaccggcg tgatcgagga gatctccgag     720
aaccgctggg acatccgccc cgtgccgcgc ttcggcaccg tggagatgcg cgtgtgcgac     780
gggccctcca acctccggga gatcggcgcc ctggccgcgc tgacgcagtg cctcgtggag     840
tccttctccc gcaccctgga cgaggggcgc agcattgcgg tgatgccccc gtggcaccac     900
caggagaaca gtggcgggc cgcccgctac gggctgacg ccgtggtgat ccggacgcc      960 cagaaccacg agcgccccgt ggcggaggac ctcaccgagg tgctcaaccg gctggagccc    1020
ctcgccgccg aactcggctg cgctgacgag ctgggctacg tggagaccat gatgacgggc    1080
gagaccggct accagcgcca gcggcggatc gcggaggcca acggcgggga cctgcgcgcc    1140
gtggtgcggg acatcgtggc gcagaaccgc gagatccgct g                        1181
```

<210> SEQ ID NO 8
<211> LENGTH: 31
<212> TYPE: DNA
<213> ORGANISM: Artificial Sequence
<220> FEATURE:
<223> OTHER INFORMATION: primer
<400> SEQUENCE: 8
aaaaggtacc atgccgttcc cggcgcaccc a                                      31

<210> SEQ ID NO 9
<211> LENGTH: 35
<212> TYPE: DNA
<213> ORGANISM: Artificial Sequence
<220> FEATURE:
<223> OTHER INFORMATION: primer
<400> SEQUENCE: 9
ttttaagctt tcagcggatc tcgcggttct gcgcc                                  35

<210> SEQ ID NO 10
<211> LENGTH: 393
<212> TYPE: PRT
<213> ORGANISM: Kocuria rhizophila
<400> SEQUENCE: 10

```
Met Pro Phe Pro Ala His Pro Arg Glu Asp His Ala Val His Ile Asp
1               5                   10                  15

Phe Glu Thr Ser Glu Asn Ser Thr Leu Gly Val Glu Trp Glu Val Ala
            20                  25                  30

Leu Val Asp Arg Glu Ser Gly Glu Leu Ala Pro Arg Ala Gln Glu Val
        35                  40                  45

Leu Glu Ala Val Val Gly Glu Tyr Pro Glu Leu Gly Glu Glu Gly Asp
```

```
                    50                  55                  60
His Pro Gln Val Thr Gly Glu Phe Leu Gln Asn Thr Val Glu Met Val
 65                  70                  75                  80

Thr Gly Val Cys Ser Ala Val Pro Glu Ala Val Glu His Leu Ala Gln
                 85                  90                  95

Thr Gln Asp Arg Ile Arg Lys Ile Thr Asp Pro Arg Ser Leu Glu Ile
            100                 105                 110

Phe Ala Ala Gly Thr His Pro Phe Ser Asp Trp Thr Glu Gln Pro Val
        115                 120                 125

Val Asp Ala Glu Arg Tyr Tyr Lys Val Leu Asp Arg Ala Gln Tyr Trp
130                 135                 140

Gly Arg Gln Met Val Ile Phe Gly Met His Val His Val Gly Ile Asp
145                 150                 155                 160

His Arg Asp Lys Ala Leu Pro Val Leu Asp Gly Leu Met Asn Tyr Tyr
                165                 170                 175

Pro His Leu Leu Ala Leu Ser Ala Asn Ser Pro Tyr Trp Cys Gly His
            180                 185                 190

Asp Thr Gly Tyr Ala Ser His Arg Ala Leu Ile Phe Gln Gln Leu Ser
        195                 200                 205

Thr Ala Gly Leu Pro Phe His Phe Asp Ser Trp Ser Glu Tyr Glu Ala
210                 215                 220

Tyr Val Ser Asp Leu Met Glu Thr Gly Val Ile Glu Glu Ile Ser Glu
225                 230                 235                 240

Asn Arg Trp Asp Ile Arg Pro Val Pro Arg Phe Gly Thr Val Glu Met
                245                 250                 255

Arg Val Cys Asp Gly Pro Ser Asn Leu Arg Glu Ile Gly Ala Leu Ala
            260                 265                 270

Ala Leu Thr Gln Cys Leu Val Glu Ser Phe Ser Arg Thr Leu Asp Glu
        275                 280                 285

Gly Arg Ser Ile Ala Val Met Pro Pro Trp His His Gln Glu Asn Lys
290                 295                 300

Trp Arg Ala Ala Arg Tyr Gly Leu Asp Ala Val Val Ile Arg Asp Ala
305                 310                 315                 320

Gln Asn His Glu Arg Pro Val Ala Glu Asp Leu Thr Glu Val Leu Asn
                325                 330                 335

Arg Leu Glu Pro Leu Ala Ala Glu Leu Gly Cys Ala Asp Glu Leu Gly
            340                 345                 350

Tyr Val Glu Thr Met Met Thr Gly Glu Thr Gly Tyr Gln Arg Gln Arg
        355                 360                 365

Arg Ile Ala Glu Ala Asn Gly Gly Asp Leu Arg Ala Val Val Arg Asp
370                 375                 380

Ile Val Ala Gln Asn Arg Glu Ile Arg
385                 390
```

<210> SEQ ID NO 11
<211> LENGTH: 1197
<212> TYPE: DNA
<213> ORGANISM: Micrococcus luteus

<400> SEQUENCE: 11
atgactctgc ccttcgccga ctccgcgcag tccactctcg aatcgagtg ggagctcgcg      60 ctcgtggacg ccgtgtccgg cgagctgcgc tccgaggccc agacctgct gcgcgccctg     120 catgtggccg agggcctggc cgacgacgac gtgaacccgc acatgaccag cgagctcctg     180

```
cagaacacgg tggagctcgt cacgggcgtg cacgagcgcg tcgacgccgc gacggcggac    240
ctcggccgga tcgccgcgcg cgtggccgac gccgcggcgg cgcggggcat ctccctgttc    300
tgccagggca cgcacccgtt cgcggacgcg atcgcgcagc cctcgacacc cagtgagcgc    360
tacgaccgca tgctggatct cacccagtac tggggtcggc agctgctgat cttcggcgtg    420
cacgtgcacg tgggcctgga cgacgtctcc aaggccatgc cggtggtgaa cggcctggtc    480
aaccgcgtgc cgcacctgct cgcactctcg gcctcctccc ccttctgggc gggcacggac    540
acgggctacc agtcccagcg cacccctcctg ttccagcagc tgcccacggc cggcctgccg    600
ttccagttcc aggagtggga ggacttcgag cgctgcgtgg cccagatgga gcaggtgggc    660
atgatcgcgg acgtcaccga gtgccgctgg gacgtgcggg ccgtgccccg cctgggcacg    720
gtggagatgc gcgcgtgtga cggcctggcc acgctcgagg agatcgccgc cgtgaccgcc    780
tacacgcagt gcctcgtgga cgatctgtcc gcgagcctgg agcgcggtga gacggtcgag    840
gtcctgccgc cgtggcacgc gcaggagaac aagtggcgcg ccgcccggta cggcatggac    900
gccaccgtga tcgtggacgc ccggggcacc caggttccgc tggcggagca cctgccggcg    960
gagatcgagc gactgacccc ggtcgccgag cggctgggct gcgaggcaga gctcgccggc   1020
gtccaggcga tgatcgacga cggcggcgcc gcgcgtcagc gtcgcgtgga ggcacaggcc   1080
ctggccggcc cgccggccga gggcgaggac gcggacgacg cggtggcccc gttgcgcgcg   1140
gtcgtgctgg acgccgccgc ccgcacccgc gcgtcgctgg acggccgcac cggctga      1197

<210> SEQ ID NO 12
<211> LENGTH: 36
<212> TYPE: DNA
<213> ORGANISM: Artificial Sequence
<220> FEATURE:
<223> OTHER INFORMATION: primer

<400> SEQUENCE: 12
aaaaggatcc atgactctgc ccttcgccga ctccgc                               36

<210> SEQ ID NO 13
<211> LENGTH: 33
<212> TYPE: DNA
<213> ORGANISM: Artificial Sequence
<220> FEATURE:
<223> OTHER INFORMATION: primer

<400> SEQUENCE: 13
ttttaagctt tcagccggtg cggccgtcca gcg                                  33

<210> SEQ ID NO 14
<211> LENGTH: 25
<212> TYPE: DNA
<213> ORGANISM: Artificial Sequence
<220> FEATURE:
<223> OTHER INFORMATION: primer

<400> SEQUENCE: 14
accgcctaca cgcagtgcct cgtgg                                           25

<210> SEQ ID NO 15
<211> LENGTH: 25
<212> TYPE: DNA
<213> ORGANISM: Artificial Sequence
<220> FEATURE:
<223> OTHER INFORMATION: primer

<400> SEQUENCE: 15
```
ccacgaggca ctgcgtgtag gcggt				25

<210> SEQ ID NO 16
<211> LENGTH: 398
<212> TYPE: PRT
<213> ORGANISM: Micrococcus luteus

<400> SEQUENCE: 16

```
Met Thr Leu Pro Phe Ala Asp Ser Ala Gln Ser Thr Leu Gly Ile Glu
 1               5                  10                  15

Trp Glu Leu Ala Leu Val Asp Ala Val Ser Gly Glu Leu Arg Ser Glu
            20                  25                  30

Ala Pro Asp Leu Leu Arg Ala Leu His Val Ala Glu Gly Leu Ala Asp
        35                  40                  45

Asp Val Asn Pro His Met Thr Ser Glu Leu Leu Gln Asn Thr Val
 50                  55                  60

Glu Leu Val Thr Gly Val His Glu Arg Val Asp Ala Ala Thr Ala Asp
 65                  70                  75                  80

Leu Gly Arg Ile Ala Ala Arg Val Ala Asp Ala Ala Ala Arg Gly
            85                  90                  95

Ile Ser Leu Phe Cys Gln Gly Thr His Pro Phe Ala Asp Ala Ile Ala
                100                 105                 110

Gln Pro Ser Thr Pro Ser Glu Arg Tyr Asp Arg Met Leu Asp Leu Thr
            115                 120                 125

Gln Tyr Trp Gly Arg Gln Leu Leu Ile Phe Gly Val His Val His Val
        130                 135                 140

Gly Leu Asp Asp Val Ser Lys Ala Met Pro Val Val Asn Gly Leu Val
145                 150                 155                 160

Asn Arg Val Pro His Leu Leu Ala Leu Ser Ala Ser Pro Phe Trp
                165                 170                 175

Ala Gly Thr Asp Thr Gly Tyr Gln Ser Gln Arg Thr Leu Leu Phe Gln
            180                 185                 190

Gln Leu Pro Thr Ala Gly Leu Pro Phe Gln Phe Gln Glu Trp Glu Asp
        195                 200                 205

Phe Glu Arg Cys Val Ala Gln Met Glu Gln Val Gly Met Ile Ala Asp
    210                 215                 220

Val Thr Glu Cys Arg Trp Asp Val Arg Ala Val Pro Arg Leu Gly Thr
225                 230                 235                 240

Val Glu Met Arg Ala Cys Asp Gly Leu Ala Thr Leu Glu Glu Ile Ala
                245                 250                 255

Ala Val Thr Ala Tyr Thr Gln Cys Leu Val Asp Asp Leu Ser Ala Ser
            260                 265                 270

Leu Glu Arg Gly Glu Thr Val Glu Val Leu Pro Pro Trp His Ala Gln
        275                 280                 285

Glu Asn Lys Trp Arg Ala Ala Arg Tyr Gly Met Asp Ala Thr Val Ile
    290                 295                 300

Val Asp Ala Arg Gly Thr Gln Val Pro Leu Ala Glu His Leu Pro Ala
305                 310                 315                 320

Glu Ile Glu Arg Leu Thr Pro Val Ala Glu Arg Leu Gly Cys Glu Ala
                325                 330                 335

Glu Leu Ala Gly Val Gln Ala Met Ile Asp Asp Gly Gly Ala Ala Arg
            340                 345                 350

Gln Arg Arg Val Glu Ala Gln Ala Leu Ala Gly Pro Pro Ala Glu Gly
        355                 360                 365
```

Glu Asp Ala Asp Asp Ala Val Ala Pro Leu Arg Ala Val Val Leu Asp
    370                 375                 380

Ala Ala Ala Arg Thr Arg Ala Ser Leu Asp Gly Arg Thr Gly
385                 390                 395

<210> SEQ ID NO 17
<211> LENGTH: 1131
<212> TYPE: DNA
<213> ORGANISM: Corynebacterium glutamicum

<400> SEQUENCE: 17

| | | | |
|---|---|---|---|
| atgggcattg agtttaagcg ttcaccgcga cccaccctgg gcgttgagtg ggaaattgca | | | 60 |
| cttgttgatc cagaaacacg tgatctagcc ccgcgcgctg cagaaatact agagattgtg | | | 120 |
| gccaagaacc accctgaggt gcacctcgag cgcgaattcc tccaaaacac cgtggagctt | | | 180 |
| gtcaccggag tgtgcgacac cgtccccgaa gcggtggcag agctttccca cgatctagat | | | 240 |
| gcgctgaaag aagcagcgga ttctctcggg cttcggttgt ggacctctgg atcccaccca | | | 300 |
| ttttcggatt ccgcgaaaa cccagtatct gaaaaggct cctacgacga gatcatcgcg | | | 360 |
| cgcacccaat actggggaaa ccagatgttg atttggggca ttcacgtcca cgtgggcatc | | | 420 |
| agccatgaag atcgcgtgtg gccgatcatc aatgcgctgc tgacaaatta cccacatctg | | | 480 |
| ttggcacttt ctgcaagctc tccagcatgg gacggacttg ataccggtta tgcctccaac | | | 540 |
| cggacgatgc tctaccaaca gctgcctaca gccggactgc ataccaattc caaagctgg | | | 600 |
| gatgaatggt gcagctacat ggcggatcaa gataaatccg gtgtcatcaa ccacaccgga | | | 660 |
| tccatgcact ttgatatccg ccccgcatcc aaatggggaa ccatcgaagt ccgcgtggcc | | | 720 |
| gattctacct ccaacctgcg ggaactgtct gccatcgtgg cgttgaccca ctgtctcgtg | | | 780 |
| gtgcactacg accgcatgat cgacgctggc gaagagcttc cctccctgca caatggcac | | | 840 |
| gtttcggaaa ataaatggcg cgcggctagg tatggtctgg atgccgaaat catcatttcc | | | 900 |
| agagacaccg atgaagcgat ggttcaagac gaactccgcc gactagtagc gcaattgatg | | | 960 |
| cctctagcca cgaactcgg ctgcgctcgt gagcttgaac ttgtgttgga atcctggaa | | | 1020 |
| cgtggtggtg gatacgaacg ccaacgcaga gtgtttaaag aaactggcag ttggaaagct | | | 1080 |
| gcagttgatt tagcctgcga cgaactcaac gacctcaaag cactggacta a | | | 1131 |

<210> SEQ ID NO 18
<211> LENGTH: 39
<212> TYPE: DNA
<213> ORGANISM: Artificial Sequence
<220> FEATURE:
<223> OTHER INFORMATION: primer

<400> SEQUENCE: 18
aaaacatatg ggcattgagt ttaagcgttc accgcgacc                                    39

<210> SEQ ID NO 19
<211> LENGTH: 29
<212> TYPE: DNA
<213> ORGANISM: Artificial Sequence
<220> FEATURE:
<223> OTHER INFORMATION: primer

<400> SEQUENCE: 19
aggaattcgc gctccaggtg cacctcagg                                               29

<210> SEQ ID NO 20

-continued

```
<211> LENGTH: 44
<212> TYPE: DNA
<213> ORGANISM: Artificial Sequence
<220> FEATURE:
<223> OTHER INFORMATION: primer

<400> SEQUENCE: 20
ttttctcgag gtccagtgct ttgaggtcgt tgagttcgtc gcag         44

<210> SEQ ID NO 21
<211> LENGTH: 29
<212> TYPE: DNA
<213> ORGANISM: Artificial Sequence
<220> FEATURE:
<223> OTHER INFORMATION: primer

<400> SEQUENCE: 21
cctgaggtgc acctggagcg cgaattcct                          29

<210> SEQ ID NO 22
<211> LENGTH: 376
<212> TYPE: PRT
<213> ORGANISM: Corynebacterium glutamicum

<400> SEQUENCE: 22
```

Met Gly Ile Glu Phe Lys Arg Ser Pro Arg Pro Thr Leu Gly Val Glu
1               5                   10                  15

Trp Glu Ile Ala Leu Val Asp Pro Glu Thr Arg Asp Leu Ala Pro Arg
            20                  25                  30

Ala Ala Glu Ile Leu Glu Ile Val Ala Lys Asn His Pro Glu Val His
        35                  40                  45

Leu Glu Arg Glu Phe Leu Gln Asn Thr Val Glu Leu Thr Gly Val
    50                  55                  60

Cys Asp Thr Val Pro Glu Ala Val Ala Glu Leu Ser His Asp Leu Asp
65                  70                  75                  80

Ala Leu Lys Glu Ala Ala Asp Ser Leu Gly Leu Arg Leu Trp Thr Ser
                85                  90                  95

Gly Ser His Pro Phe Ser Asp Phe Arg Glu Asn Pro Val Ser Glu Lys
            100                 105                 110

Gly Ser Tyr Asp Glu Ile Ile Ala Arg Thr Gln Tyr Trp Gly Asn Gln
        115                 120                 125

Met Leu Ile Trp Gly Ile His Val His Val Gly Ile Ser His Glu Asp
    130                 135                 140

Arg Val Trp Pro Ile Ile Asn Ala Leu Leu Thr Asn Tyr Pro His Leu
145                 150                 155                 160

Leu Ala Leu Ser Ala Ser Ser Pro Ala Trp Asp Gly Leu Asp Thr Gly
                165                 170                 175

Tyr Ala Ser Asn Arg Thr Met Leu Tyr Gln Gln Leu Pro Thr Ala Gly
            180                 185                 190

Leu Pro Tyr Gln Phe Gln Ser Trp Asp Glu Trp Cys Ser Tyr Met Ala
        195                 200                 205

Asp Gln Asp Lys Ser Gly Val Ile Asn His Thr Gly Ser Met His Phe
    210                 215                 220

Asp Ile Arg Pro Ala Ser Lys Trp Gly Thr Ile Glu Val Arg Val Ala
225                 230                 235                 240

Asp Ser Thr Ser Asn Leu Arg Glu Leu Ser Ala Ile Val Ala Leu Thr
                245                 250                 255

His Cys Leu Val Val His Tyr Asp Arg Met Ile Asp Ala Gly Glu Glu

```
            260                 265                 270
Leu Pro Ser Leu Gln Gln Trp His Val Ser Glu Asn Lys Trp Arg Ala
        275                 280                 285

Ala Arg Tyr Gly Leu Asp Ala Glu Ile Ile Ile Ser Arg Asp Thr Asp
        290                 295                 300

Glu Ala Met Val Gln Asp Glu Leu Arg Arg Leu Val Ala Gln Leu Met
305                 310                 315                 320

Pro Leu Ala Asn Glu Leu Gly Cys Ala Arg Glu Leu Glu Leu Val Leu
                325                 330                 335

Glu Ile Leu Glu Arg Gly Gly Gly Tyr Glu Arg Gln Arg Arg Val Phe
                340                 345                 350

Lys Glu Thr Gly Ser Trp Lys Ala Ala Val Asp Leu Ala Cys Asp Glu
            355                 360                 365

Leu Asn Asp Leu Lys Ala Leu Asp
        370                 375

<210> SEQ ID NO 23
<211> LENGTH: 2037
<212> TYPE: DNA
<213> ORGANISM: Saccharomyces cerevisiae

<400> SEQUENCE: 23
```

| | | | | |
|---|---|---|---|---|
| atgggactct tagctttggg cacgcctttg cagtggtttg agtctaggac gtacaatgaa | | | | 60 |
| cacataaggg atgaaggtat cgagcagttg ttgtatattt tccaagctgc tggtaaaaga | | | | 120 |
| gacaatgacc ctcttttttg gggagacgag cttgagtaca tggttgtaga ttttgatgat | | | | 180 |
| aaggagagaa attctatgct cgacgtttgc catgacaaga tactcactga gcttaatatg | | | | 240 |
| gaggattcgt ccctttgtga ggctaacgat gtgagttttc accctgagta tggccggtat | | | | 300 |
| atgttagagg caacaccagc ttctccatat ttgaattacg tgggtagtta cgttgaggtt | | | | 360 |
| aacatgcaaa aaagacgtgc cattgcagaa tataagctat ctgaatatgc gagacaagat | | | | 420 |
| agtaaaaata acttgcatgt gggctccagg tctgtcccct tgacgctgac tgtcttcccg | | | | 480 |
| aggatgggat gccccgactt tattaacatt aaggatccgt ggaatcataa aaatgccgct | | | | 540 |
| tccaggtctc tgtttttacc cgatgaagtc attaacagac atgtcaggtt tcctaacttg | | | | 600 |
| acagcatcca tcaggaccag gcgtggtgaa aaagtttgca tgaatgttcc catgtataaa | | | | 660 |
| gatatagcta ctccagaaac ggatgactcc atctacgatc gagattggtt tttaccagaa | | | | 720 |
| gacaaagagg cgaaactggc ttccaaaccg ggtttcattt atatggattc catgggtttt | | | | 780 |
| ggcatgggct gttcgtgctt acaagtgacc tttcaggcac ccaatatcaa caaggcacgt | | | | 840 |
| tacctgtacg atgcattagt gaattttgca cctataatgc tagccttctc tgccgctgcg | | | | 900 |
| cctgctttta aaggttggct agccgaccaa gatgttcgtt ggaatgtgat atctggtgcg | | | | 960 |
| gtggacgacc gtactccgaa ggaaagaggt gttgcgccat actacccaa atacaacaag | | | | 1020 |
| aacggatttg gaggcattgc caaagacgta caagataaag tccttgaaat accaaagtca | | | | 1080 |
| agatatagtt cggttgatct tttcttgggt gggtcgaaat ttttcaatag gacttataac | | | | 1140 |
| gacacaaatg tacctattaa tgaaaaagta ttaggacgac tactagagaa tgataaggcg | | | | 1200 |
| ccactggact atgatcttgc taaacatttt gcgcatctct acataagaga tccagtatct | | | | 1260 |
| acattcgaag aactgttgaa tcaggacaac aaaacgtctt caaatcactt tgaaaacatc | | | | 1320 |
| caaagtacaa attggcagac attcgttttt aaacccccca cacaacaagc aaccccggac | | | | 1380 |
| aaaaaggatt ctcctggttg gagagtggaa ttcagaccat ttgaagtgca actattagat | | | | 1440 |

-continued

```
tttgagaacg ctgcgtattc cgtgctcata tacttgattg tcgatagcat tttgaccttt    1500
tccgataata ttaacgcata tattcatatg tccaaagtat gggaaaatat gaagatagcc    1560
catcacagag atgctatcct atttgaaaaa tttcattgga aaaaatcatt tcgcaacgac    1620
accgatgtgg aaactgaaga ttattctata agcgagattt tccataatcc agagaatggt    1680
atatttcctc aatttgttac gccaatccta tgccaaaaag ggtttgtaac caaagattgg    1740
aaagaattaa agcattcttc caaacacgag agactatact attatttaaa gctaatttct    1800
gatagagcaa gcggtgaatt gccaacaaca gcaaaattct ttagaaattt tgtactacaa    1860
catccagatt acaaacatga ttcaaaaatt tcaaagtcga tcaattatga tttgctttct    1920
acgtgtgata gacttaccca tttagacgat tcaaaaggtg aattgacatc ctttttagga    1980
gctgaaattg cagaatatgt aaaaaaaaat aagccttcaa tagaaagcaa atgttaa      2037
```

<210> SEQ ID NO 24
<211> LENGTH: 678
<212> TYPE: PRT
<213> ORGANISM: Saccharomyces cerevisiae

<400> SEQUENCE: 24

```
Met Gly Leu Leu Ala Leu Gly Thr Pro Leu Gln Trp Phe Glu Ser Arg
1               5                   10                  15

Thr Tyr Asn Glu His Ile Arg Asp Glu Gly Ile Glu Gln Leu Leu Tyr
            20                  25                  30

Ile Phe Gln Ala Ala Gly Lys Arg Asp Asn Asp Pro Leu Phe Trp Gly
        35                  40                  45

Asp Glu Leu Glu Tyr Met Val Val Asp Phe Asp Asp Lys Glu Arg Asn
    50                  55                  60

Ser Met Leu Asp Val Cys His Asp Lys Ile Leu Thr Glu Leu Asn Met
65                  70                  75                  80

Glu Asp Ser Ser Leu Cys Glu Ala Asn Asp Val Ser Phe His Pro Glu
                85                  90                  95

Tyr Gly Arg Tyr Met Leu Glu Ala Thr Pro Ala Ser Pro Tyr Leu Asn
            100                 105                 110

Tyr Val Gly Ser Tyr Val Glu Val Asn Met Gln Lys Arg Arg Ala Ile
        115                 120                 125

Ala Glu Tyr Lys Leu Ser Glu Tyr Ala Arg Gln Asp Ser Lys Asn Asn
    130                 135                 140

Leu His Val Gly Ser Arg Ser Val Pro Leu Thr Leu Thr Val Phe Pro
145                 150                 155                 160

Arg Met Gly Cys Pro Asp Phe Ile Asn Ile Lys Asp Pro Trp Asn His
                165                 170                 175

Lys Asn Ala Ala Ser Arg Ser Leu Phe Leu Pro Asp Glu Val Ile Asn
            180                 185                 190

Arg His Val Arg Phe Pro Asn Leu Thr Ala Ser Ile Arg Thr Arg Arg
        195                 200                 205

Gly Glu Lys Val Cys Met Asn Val Pro Met Tyr Lys Asp Ile Ala Thr
    210                 215                 220

Pro Glu Thr Asp Asp Ser Ile Tyr Asp Arg Asp Trp Phe Leu Pro Glu
225                 230                 235                 240

Asp Lys Glu Ala Lys Leu Ala Ser Lys Pro Gly Phe Ile Tyr Met Asp
                245                 250                 255

Ser Met Gly Phe Gly Met Gly Cys Ser Cys Leu Gln Val Thr Phe Gln
            260                 265                 270
```

```
Ala Pro Asn Ile Asn Lys Ala Arg Tyr Leu Tyr Asp Ala Leu Val Asn
        275                 280                 285
Phe Ala Pro Ile Met Leu Ala Phe Ser Ala Ala Pro Ala Phe Lys
290                 295                 300
Gly Trp Leu Ala Asp Gln Asp Val Arg Trp Asn Val Ile Ser Gly Ala
305                 310                 315                 320
Val Asp Asp Arg Thr Pro Lys Glu Arg Gly Val Ala Pro Leu Leu Pro
                325                 330                 335
Lys Tyr Asn Lys Asn Gly Phe Gly Gly Ile Ala Lys Asp Val Gln Asp
                340                 345                 350
Lys Val Leu Glu Ile Pro Lys Ser Arg Tyr Ser Ser Val Asp Leu Phe
                355                 360                 365
Leu Gly Gly Ser Lys Phe Phe Asn Arg Thr Tyr Asn Asp Thr Asn Val
                370                 375                 380
Pro Ile Asn Glu Lys Val Leu Gly Arg Leu Leu Glu Asn Asp Lys Ala
385                 390                 395                 400
Pro Leu Asp Tyr Asp Leu Ala Lys His Phe Ala His Leu Tyr Ile Arg
                405                 410                 415
Asp Pro Val Ser Thr Phe Glu Glu Leu Leu Asn Gln Asp Asn Lys Thr
                420                 425                 430
Ser Ser Asn His Phe Glu Asn Ile Gln Ser Thr Asn Trp Gln Thr Leu
                435                 440                 445
Arg Phe Lys Pro Pro Thr Gln Gln Ala Thr Pro Asp Lys Lys Asp Ser
    450                 455                 460
Pro Gly Trp Arg Val Glu Phe Arg Pro Phe Glu Val Gln Leu Leu Asp
465                 470                 475                 480
Phe Glu Asn Ala Ala Tyr Ser Val Leu Ile Tyr Leu Ile Val Asp Ser
                485                 490                 495
Ile Leu Thr Phe Ser Asp Asn Ile Asn Ala Tyr Ile His Met Ser Lys
                500                 505                 510
Val Trp Glu Asn Met Lys Ile Ala His His Arg Asp Ala Ile Leu Phe
                515                 520                 525
Glu Lys Phe His Trp Lys Lys Ser Phe Arg Asn Asp Thr Asp Val Glu
        530                 535                 540
Thr Glu Asp Tyr Ser Ile Ser Glu Ile Phe His Asn Pro Glu Asn Gly
545                 550                 555                 560
Ile Phe Pro Gln Phe Val Thr Pro Ile Leu Cys Gln Lys Gly Phe Val
                565                 570                 575
Thr Lys Asp Trp Lys Glu Leu Lys His Ser Ser Lys His Glu Arg Leu
                580                 585                 590
Tyr Tyr Tyr Leu Lys Leu Ile Ser Asp Arg Ala Ser Gly Glu Leu Pro
                595                 600                 605
Thr Thr Ala Lys Phe Phe Arg Asn Phe Val Leu Gln His Pro Asp Tyr
        610                 615                 620
Lys His Asp Ser Lys Ile Ser Lys Ser Ile Asn Tyr Asp Leu Leu Ser
625                 630                 635                 640
Thr Cys Asp Arg Leu Thr His Leu Asp Asp Ser Lys Gly Glu Leu Thr
                645                 650                 655
Ser Phe Leu Gly Ala Glu Ile Ala Glu Tyr Val Lys Lys Asn Lys Pro
                660                 665                 670
Ser Ile Glu Ser Lys Cys
                675
```

<210> SEQ ID NO 25
<211> LENGTH: 1557
<212> TYPE: DNA
<213> ORGANISM: Escherichia coli

<400> SEQUENCE: 25

| | | | | | |
|---|---|---|---|---|---|
| ttgatcccgg | acgtatcaca | ggcgctggcc | tggctggaaa | acatcctca | ggcgttaaag | 60 |
| gggatacagc | gtgggctgga | gcgcgaaact | ttgcgtgtta | atgctgatgg | cacactggca | 120 |
| acaacaggtc | atcctgaagc | attaggttcc | gcactgacgc | acaaatggat | tactaccgat | 180 |
| tttgcggaag | cattgctgga | attcattaca | ccagtggatg | gtgatattga | acatatgctg | 240 |
| acctttatgc | gcgatctgca | tcgttatacg | gcgcgcaata | tgggcgatga | gcggatgtgg | 300 |
| ccgttaagta | tgccatgcta | catcgcagaa | ggtcaggaca | tcgaactggc | acagtacggc | 360 |
| acttctaaca | ccggacgctt | taaaacgctg | tatcgtgaag | ggctgaaaaa | tcgctacggc | 420 |
| gcgctgatgc | aaaccatttc | cggcgtgcac | tacaatttct | ctttgccaat | ggcattctgg | 480 |
| caagcgaagt | gcggtgatat | ctcgggcgct | gatgccaaag | agaaaatttc | tgcgggctat | 540 |
| ttccgcgtta | tccgcaatta | ctatcgtttc | ggtttgggtca | ttccttatct | gtttggtgca | 600 |
| tctccggcga | tttgttcttc | tttcctgcaa | ggaaaaaccaa | cgtcgctgcc | gtttgagaaa | 660 |
| accgagtgcg | gtatgtatta | cctgccgtat | gcgacctctc | ttcgtttgag | cgatctcggc | 720 |
| tataccaata | aatcgcaaag | caatcttggt | attaccttca | acgatcttta | cgagtacgta | 780 |
| gcgggcctta | acaggcaat | caaaacgcca | tcggaagagt | acgcgaagat | tggtattgag | 840 |
| aaagacggta | agaggctgca | aatcaacagc | aacgtgttgc | agattgaaaa | cgaactgtac | 900 |
| gcgccgattc | gtccaaaacg | cgttacccgc | agcggcgagt | cgccttctga | tgcgctgtta | 960 |
| cgtggcggca | ttgaatatat | tgaagtgcgt | tcgctggaca | tcaacccgtt | ctcgccgatt | 1020 |
| ggtgtagatg | aacagcaggt | gcgattcctc | gacctgttta | tggtctggtg | tgcgctggct | 1080 |
| gatgcaccgg | aaatgagcag | tagcgaactt | gcctgtacac | gcgttaactg | gaaccgggtg | 1140 |
| atcctcgaag | gtcgcaaacc | gggtctgacg | ctgggtatcg | gctgcgaaac | cgcacagttc | 1200 |
| ccgttaccgc | aggtgggtaa | agatctgttc | cgcgatctga | aacgcgtcgc | gcaaacgctg | 1260 |
| gatagtatta | acggcggcga | agcgtatcag | aaagtgtgtg | atgaactggt | tgcctgcttc | 1320 |
| gataatcccg | atctgacttt | ctctgcccgt | atcttaaggt | ctatgattga | tactggtatt | 1380 |
| ggcggaacag | gcaaagcatt | tgcagaagcc | taccgtaatc | tgctgcgtga | agagccgctg | 1440 |
| gaaattctgc | gcgaagagga | ttttgtagcc | gagcgcgagg | cgtctgaacg | ccgtcagcag | 1500 |
| gaaatggaag | ccgctgatac | cgaaccgttt | gcggtgtggc | tggaaaaaca | cgcctga | 1557 |

<210> SEQ ID NO 26
<211> LENGTH: 518
<212> TYPE: PRT
<213> ORGANISM: Escherichia coli

<400> SEQUENCE: 26

Met Ile Pro Asp Val Ser Gln Ala Leu Ala Trp Leu Glu Lys His Pro
1               5                   10                  15

Gln Ala Leu Lys Gly Ile Gln Arg Gly Leu Glu Arg Glu Thr Leu Arg
            20                  25                  30

Val Asn Ala Asp Gly Thr Leu Ala Thr Thr Gly His Pro Glu Ala Leu
        35                  40                  45

Gly Ser Ala Leu Thr His Lys Trp Ile Thr Thr Asp Phe Ala Glu Ala
    50                  55                  60

```
Leu Leu Glu Phe Ile Thr Pro Val Asp Gly Asp Ile Glu His Met Leu
 65                  70                  75                  80

Thr Phe Met Arg Asp Leu His Arg Tyr Thr Ala Arg Asn Met Gly Asp
                 85                  90                  95

Glu Arg Met Trp Pro Leu Ser Met Pro Cys Tyr Ile Ala Glu Gly Gln
            100                 105                 110

Asp Ile Glu Leu Ala Gln Tyr Gly Thr Ser Asn Thr Gly Arg Phe Lys
        115                 120                 125

Thr Leu Tyr Arg Glu Gly Leu Lys Asn Arg Tyr Gly Ala Leu Met Gln
130                 135                 140

Thr Ile Ser Gly Val His Tyr Asn Phe Ser Leu Pro Met Ala Phe Trp
145                 150                 155                 160

Gln Ala Lys Cys Gly Asp Ile Ser Gly Ala Asp Ala Lys Glu Lys Ile
                165                 170                 175

Ser Ala Gly Tyr Phe Arg Val Ile Arg Asn Tyr Tyr Arg Phe Gly Trp
            180                 185                 190

Val Ile Pro Tyr Leu Phe Gly Ala Ser Pro Ala Ile Cys Ser Ser Phe
        195                 200                 205

Leu Gln Gly Lys Pro Thr Ser Leu Pro Phe Glu Lys Thr Glu Cys Gly
210                 215                 220

Met Tyr Tyr Leu Pro Tyr Ala Thr Ser Leu Arg Leu Ser Asp Leu Gly
225                 230                 235                 240

Tyr Thr Asn Lys Ser Gln Ser Asn Leu Gly Ile Thr Phe Asn Asp Leu
                245                 250                 255

Tyr Glu Tyr Val Ala Gly Leu Lys Gln Ala Ile Lys Thr Pro Ser Glu
            260                 265                 270

Glu Tyr Ala Lys Ile Gly Ile Glu Lys Asp Gly Lys Arg Leu Gln Ile
        275                 280                 285

Asn Ser Asn Val Leu Gln Ile Glu Asn Glu Leu Tyr Ala Pro Ile Arg
290                 295                 300

Pro Lys Arg Val Thr Arg Ser Gly Glu Ser Pro Ser Asp Ala Leu Leu
305                 310                 315                 320

Arg Gly Gly Ile Glu Tyr Ile Glu Val Arg Ser Leu Asp Ile Asn Pro
                325                 330                 335

Phe Ser Pro Ile Gly Val Asp Glu Gln Gln Val Arg Phe Leu Asp Leu
            340                 345                 350

Phe Met Val Trp Cys Ala Leu Ala Asp Ala Pro Glu Met Ser Ser Ser
        355                 360                 365

Glu Leu Ala Cys Thr Arg Val Asn Trp Asn Arg Val Ile Leu Glu Gly
370                 375                 380

Arg Lys Pro Gly Leu Thr Leu Gly Ile Gly Cys Glu Thr Ala Gln Phe
385                 390                 395                 400

Pro Leu Pro Gln Val Gly Lys Asp Leu Phe Arg Asp Leu Lys Arg Val
                405                 410                 415

Ala Gln Thr Leu Asp Ser Ile Asn Gly Gly Glu Ala Tyr Gln Lys Val
            420                 425                 430

Cys Asp Glu Leu Val Ala Cys Phe Asp Asn Pro Asp Leu Thr Phe Ser
        435                 440                 445

Ala Arg Ile Leu Arg Ser Met Ile Asp Thr Gly Ile Gly Gly Thr Gly
450                 455                 460

Lys Ala Phe Ala Glu Ala Tyr Arg Asn Leu Leu Arg Glu Glu Pro Leu
465                 470                 475                 480

Glu Ile Leu Arg Glu Glu Asp Phe Val Ala Glu Arg Glu Ala Ser Glu
```

```
                485             490             495
Arg Arg Gln Gln Glu Met Glu Ala Ala Asp Thr Glu Pro Phe Ala Val
        500                 505                 510
Trp Leu Glu Lys His Ala
        515

<210> SEQ ID NO 27
<211> LENGTH: 951
<212> TYPE: DNA
<213> ORGANISM: Escherichia coli

<400> SEQUENCE: 27
atgatcaagc tcggcatcgt gatggacccc atcgcaaaca tcaacatcaa gaaagattcc      60
agttttgcta tgttgctgga agcacagcgt cgtggttacg aacttcacta tatggagatg     120
ggcgatctgt atctgatcaa tggtgaagcc cgcgcccata cccgcacgct gaacgtgaag     180
cagaactacg aagagtggtt ttcgttcgtc ggtgaacagg atctgccgct ggccgatctc     240
gatgtgatcc tgatgcgtaa agacccgccg tttgataccg agtttatcta cgcgacctat     300
attctggaac gtgccgaaga gaagggacg ctgatcgtta acaagccgca gagcctgcgc     360
gactgtaacg agaaactgtt taccgcctgg ttctctgact aacgccagaa acgctggtt     420 acgcgcaata agcgcagct aaaagcgttc tgggagaaac acagcgacat cattcttaag     480
ccgctggacg gtatgggcgg cgcgtcgatt ttccgcgtga agaaggcga tccaaacctc     540 ggcgtgattg ccgaaaccct gactgagcat ggcactcgct actgcatggc gcaaaattac     600
ctgccagcca ttaaagatgg cgacaaacgc gtgctggtgg tggatggcga gccggtaccg     660
tactgcctgg cgcgtattcc gcaggggggc gaaacccgtg gcaatctggc tgccggtggt     720
cgcggtgaac ctcgtccgct gacggaaagt gactggaaaa tcgcccgtca gatcgggccg     780
acgctgaaag aaaaagggct gattttttgtt ggtctggata tcatcggcga ccgtctgact     840
gaaattaacg tcaccagccc aacctgtatt cgtgagattg aagcagagtt tccggtgtcg     900
atcaccggaa tgttaatgga tgccatcgaa gcacgtttac agcagcagta a             951

<210> SEQ ID NO 28
<211> LENGTH: 316
<212> TYPE: PRT
<213> ORGANISM: Escherichia coli

<400> SEQUENCE: 28

Met Ile Lys Leu Gly Ile Val Met Asp Pro Ile Ala Asn Ile Asn Ile
1               5                   10                  15

Lys Lys Asp Ser Ser Phe Ala Met Leu Leu Glu Ala Gln Arg Arg Gly
            20                  25                  30

Tyr Glu Leu His Tyr Met Glu Met Gly Asp Leu Tyr Leu Ile Asn Gly
        35                  40                  45

Glu Ala Arg Ala His Thr Arg Thr Leu Asn Val Lys Gln Asn Tyr Glu
    50                  55                  60

Glu Trp Phe Ser Phe Val Gly Glu Gln Asp Leu Pro Leu Ala Asp Leu
65                  70                  75                  80

Asp Val Ile Leu Met Arg Lys Asp Pro Pro Phe Asp Thr Glu Phe Ile
                85                  90                  95

Tyr Ala Thr Tyr Ile Leu Glu Arg Ala Glu Glu Lys Gly Thr Leu Ile
            100                 105                 110

Val Asn Lys Pro Gln Ser Leu Arg Asp Cys Asn Glu Lys Leu Phe Thr
        115                 120                 125
```

-continued

```
Ala Trp Phe Ser Asp Leu Thr Pro Glu Thr Leu Val Thr Arg Asn Lys
    130                 135                 140

Ala Gln Leu Lys Ala Phe Trp Glu Lys His Ser Asp Ile Ile Leu Lys
145                 150                 155                 160

Pro Leu Asp Gly Met Gly Gly Ala Ser Ile Phe Arg Val Lys Glu Gly
                165                 170                 175

Asp Pro Asn Leu Gly Val Ile Ala Glu Thr Leu Thr Glu His Gly Thr
            180                 185                 190

Arg Tyr Cys Met Ala Gln Asn Tyr Leu Pro Ala Ile Lys Asp Gly Asp
        195                 200                 205

Lys Arg Val Leu Val Asp Gly Glu Pro Val Pro Tyr Cys Leu Ala
    210                 215                 220

Arg Ile Pro Gln Gly Gly Glu Thr Arg Gly Asn Leu Ala Ala Gly Gly
225                 230                 235                 240

Arg Gly Glu Pro Arg Pro Leu Thr Glu Ser Asp Trp Lys Ile Ala Arg
                245                 250                 255

Gln Ile Gly Pro Thr Leu Lys Glu Lys Gly Leu Ile Phe Val Gly Leu
            260                 265                 270

Asp Ile Ile Gly Asp Arg Leu Thr Glu Ile Asn Val Thr Ser Pro Thr
        275                 280                 285

Cys Ile Arg Glu Ile Glu Ala Glu Phe Pro Val Ser Ile Thr Gly Met
    290                 295                 300

Leu Met Asp Ala Ile Glu Ala Arg Leu Gln Gln Gln
305                 310                 315

<210> SEQ ID NO 29
<211> LENGTH: 1743
<212> TYPE: DNA
<213> ORGANISM: Escherichia coli

<400> SEQUENCE: 29
atgataaaac cgacgttttt acgccgggtg gccattgctg ctctgctctc aggaagttgt      60
tttagcgccg ccgccgcgcc tcctgcgccc cccgtctcgt atggtgtgga ggaagatgtc     120
ttccacccgg tacgcgcgaa acagggaatg gtagcgtctc tggacgccac tgccactcag     180 gtggggggtgg atattctcaa ggagggcggg aatgccgttg atgccgccgt ggcggtgggc    240
tacgcgctgg cggtaacgca tccgcaggca gggaatctgg cggtggtggt ttttatgtta    300
atccgctcga aaatggcaa taccacggct atcgatttcc gcgaaatggc acccgccaaa     360
gcgaccgccg atatgttcct cgatgatcag ggcaacccgg acagcaaaaa atcactcact     420
tcgcatctgg cttccggcac accgggtacg gtagcaggtt tctcgctggc gctggataaa     480
tacggcacca tgccgctgaa caaagtcgtg cagcccgcgt ttaaactggc acgcgatggt    540
tttatcgtta cgacgcgct ggctgacgat ctcaaaacct acggtagcga agtgttgccg      600
aatcacgaaa acagtaaagc tatcttctgg aaagagggcg agccgctgaa aagggcgac     660 acgctggtgc aggcgaacct ggcaaagagc ctggagatga ttgctgaaaa cggcccggac    720
gaattctata aaggcacgat tgcggaacag atcgcccagg agatgcagaa aaacggtggc    780
ttgatcacta agaagattt agcagccat aaagcggtcg aacgcactcc gataagcggc     840
gattatcgcg gtatcaggt ttactccatg ccaccgccat cctccggcgg atccatatc     900 gtacaaatcc tcaatattct ggaaaacttc gatatgaaga atacggcttg gcagcgcc     960 gatgcgatgc aaatcatggc agaagcggag aaatacgcct acgccgaccg ctcggaatat    1020
```

```
cttggcgacc cggattttgt caaagtaccg tggcaggcgc tgaccaataa agcctatgcc    1080
aaatctattg ccgatcaaat tgatatcaat aaagcgaagc catccagcga aattcgcccc    1140
ggcaagcttg cgccttatga gagtaatcaa actacccatt actcagtggt ggataaagat    1200
ggtaacgcgg tggcggtgac ctatacgctg aacaccacct tcggtacggg cattgtcgcg    1260
ggcgagagcg gtattctgct taataaccag atggatgatt tctccgccaa accgggcgta    1320
ccgaacgttt acgggctggt gggcggtgat gccaacgccg tcgggccgaa caaacgcccg    1380
ctgtcgtcga tgtcgccgac cattgtggtg aaagacggta aaacctggct ggttaccggt    1440
agcccaggcg gtagccggat catcactaca gtgctgcaaa tggtggtgaa tagcatcgat    1500
tatggcttga acgtcgccga agcgaccaat gcgccgcgtt ccaccatca gtggttgccg    1560 gacgagctgc gtgtcgaaaa agggtttagc ccggatacgc tcaagctgct ggaagcaaaa    1620
ggtcagaaag tggcgctgaa agaggcgatg ggcagtacac aaagcattat ggttgggccg    1680
gacggtgagt tgtacggcgc atccgacccg cgctcggtgg atgatttaac ggcggggtac    1740
taa                                                                  1743
```

<210> SEQ ID NO 30
<211> LENGTH: 580
<212> TYPE: PRT
<213> ORGANISM: Escherichia coli

<400> SEQUENCE: 30

```
Met Ile Lys Pro Thr Phe Leu Arg Arg Val Ala Ile Ala Ala Leu Leu
1               5                   10                  15

Ser Gly Ser Cys Phe Ser Ala Ala Ala Pro Ala Pro Pro Val
            20                  25                  30

Ser Tyr Gly Val Glu Glu Asp Val Phe His Pro Val Arg Ala Lys Gln
        35                  40                  45

Gly Met Val Ala Ser Val Asp Ala Thr Ala Gln Val Gly Val Asp
    50                  55                  60

Ile Leu Lys Glu Gly Gly Asn Ala Val Asp Ala Val Ala Val Gly
65                  70                  75                  80

Tyr Ala Leu Ala Val Thr His Pro Gln Ala Gly Asn Leu Gly Gly Gly
                85                  90                  95

Gly Phe Met Leu Ile Arg Ser Lys Asn Gly Asn Thr Thr Ala Ile Asp
            100                 105                 110

Phe Arg Glu Met Ala Pro Ala Lys Ala Thr Arg Asp Met Phe Leu Asp
        115                 120                 125

Asp Gln Gly Asn Pro Asp Ser Lys Lys Ser Leu Thr Ser His Leu Ala
    130                 135                 140

Ser Gly Thr Pro Gly Thr Val Ala Gly Phe Ser Leu Ala Leu Asp Lys
145                 150                 155                 160

Tyr Gly Thr Met Pro Leu Asn Lys Val Val Gln Pro Ala Phe Lys Leu
                165                 170                 175

Ala Arg Asp Gly Phe Ile Val Asn Asp Ala Leu Ala Asp Leu Lys
            180                 185                 190

Thr Tyr Gly Ser Glu Val Leu Pro Asn His Glu Asn Ser Lys Ala Ile
        195                 200                 205

Phe Trp Lys Glu Gly Glu Pro Leu Lys Lys Gly Asp Thr Leu Val Gln
    210                 215                 220

Ala Asn Leu Ala Lys Ser Leu Glu Met Ile Ala Glu Asn Gly Pro Asp
225                 230                 235                 240
```

```
Glu Phe Tyr Lys Gly Thr Ile Ala Glu Gln Ile Ala Gln Glu Met Gln
                245                 250                 255

Lys Asn Gly Gly Leu Ile Thr Lys Glu Asp Leu Ala Ala Tyr Lys Ala
            260                 265                 270

Val Glu Arg Thr Pro Ile Ser Gly Asp Tyr Arg Gly Tyr Gln Val Tyr
        275                 280                 285

Ser Met Pro Pro Ser Ser Gly Gly Ile His Ile Val Gln Ile Leu
    290                 295                 300

Asn Ile Leu Glu Asn Phe Asp Met Lys Lys Tyr Gly Phe Gly Ser Ala
305                 310                 315                 320

Asp Ala Met Gln Ile Met Ala Glu Ala Glu Lys Tyr Ala Tyr Ala Asp
                325                 330                 335

Arg Ser Glu Tyr Leu Gly Asp Pro Asp Phe Val Lys Val Pro Trp Gln
                340                 345                 350

Ala Leu Thr Asn Lys Ala Tyr Ala Lys Ser Ile Ala Asp Gln Ile Asp
                355                 360                 365

Ile Asn Lys Ala Lys Pro Ser Ser Glu Ile Arg Pro Gly Lys Leu Ala
        370                 375                 380

Pro Tyr Glu Ser Asn Gln Thr Thr His Tyr Ser Val Val Asp Lys Asp
385                 390                 395                 400

Gly Asn Ala Val Ala Val Thr Tyr Thr Leu Asn Thr Thr Phe Gly Thr
                405                 410                 415

Gly Ile Val Ala Gly Glu Ser Gly Ile Leu Leu Asn Asn Gln Met Asp
                420                 425                 430

Asp Phe Ser Ala Lys Pro Gly Val Pro Asn Val Tyr Gly Leu Val Gly
        435                 440                 445

Gly Asp Ala Asn Ala Val Gly Pro Asn Lys Arg Pro Leu Ser Ser Met
    450                 455                 460

Ser Pro Thr Ile Val Val Lys Asp Gly Lys Thr Trp Leu Val Thr Gly
465                 470                 475                 480

Ser Pro Gly Gly Ser Arg Ile Ile Thr Thr Val Leu Gln Met Val Val
                485                 490                 495

Asn Ser Ile Asp Tyr Gly Leu Asn Val Ala Glu Ala Thr Asn Ala Pro
            500                 505                 510

Arg Phe His His Gln Trp Leu Pro Asp Glu Leu Arg Val Glu Lys Gly
        515                 520                 525

Phe Ser Pro Asp Thr Leu Lys Leu Leu Glu Ala Lys Gly Gln Lys Val
    530                 535                 540

Ala Leu Lys Glu Ala Met Gly Ser Thr Gln Ser Ile Met Val Gly Pro
545                 550                 555                 560

Asp Gly Glu Leu Tyr Gly Ala Ser Asp Pro Arg Ser Val Asp Asp Leu
                565                 570                 575

Thr Ala Gly Tyr
            580
```

GAMMA GLUTAMYL-VALINE SYNTHASE, AND METHOD FOR PRODUCING GAMMA GLUTAMYL-VALYL-GLYCINE

TECHNICAL FIELD

The present invention relates to γ-glutamylvaline synthetase (γ-Glu-Val synthetase) and a method for producing γ-glutamylvalylglycine using the same. γ-Glutamylvalylglycine is useful in the fields of food, drug, and so forth.

BACKGROUND ART

Certain kinds of peptides such as γ-glutamylvalylglycine (L-γ-glutamyl-L-valyl-glycine, henceforth also referred to as "γ-Glu-Val-Gly") have a calcium sensing receptor agonist activity (Patent document 1). Such peptides having a calcium receptor agonist activity are known to be able to impart "kokumi" to foods and drinks (Patent document 2), improve tastes of low fat foods, especially fat-like thickness and smoothness (Patent document 3), improve feeling of body of sweet taste substances, and improve bitterness peculiar to sweet taste substances (Patent document 4).

Moreover, such peptides as mentioned above are known to have a prophylactic or curative effect on diarrhea (Patent document 5) and diabetes (Patent document 6), and a bicarbonate secretion promoting effect in the alimentary tract (Patent document 7).

As methods for producing γ-glutamyl tripeptides, chemical synthesis methods and enzymatic methods are generally known. As one of the chemical synthesis methods, a method of selectively obtaining a γ-glutamyl tripeptide from a dipeptide by using N-protected glutamic anhydride is known (Patent document 8). As one of the enzymatic methods, there is known a method of using glutamate-cysteine ligase (GSHA) and glutathione synthetase (GSHB) is known (Patent documents 9 and 10). As another enzymatic method, there is also known a method of γ-glutamylating Val-Gly by using γ-glutamyltransferase to generate γ-Glu-Val-Gly (Patent document 11).

Glutamate-cysteine ligase (GSHA) is known as an enzyme having an activity for catalyzing the reaction of generating γ-Glu-Cys, ADP, and phosphate using Glu, Cys, and ATP as substrates (EC 6.3.2.2). GSHA usually requires divalent metal ions such as $Mg^{2+}$ and $Mn^{2+}$ for the enzymatic reaction.

GSHA of *Escherichia coli* generates γ-glutamyl dipeptides using Glu, various kinds of amino acids, and ATP as substrates in the presence of $Mg^2$ or $Mn^{2+}$, and it is known that type of the metal ion serving as a cofactor affects the substrate specificity thereof (Non-patent document 1). Specifically, it has been reported that when $Mg^{2+}$ is used as the cofactor, Vmax is 251 mol/mg/hr and Km is 17.6 mM as for the γ-Glu-Gly generation activity, whereas Vmax is 59 mol/mg/hr and Km is 27.1 mM as for the γ-Glu-Val generation activity. That is, if the activities are compared by using Vmax/Km as index of the activities, the ratio of γ-Glu-Val generation activity to the γ-Glu-Gly generation activity in the case of using $Mg^{2+}$ as the cofactor can be calculated to be 0.15. Further, it has been demonstrated that when $Mn^{2+}$ is used as the cofactor, Vmax is 39 mol/mg/hr and Km is 1.7 mM as for the γ-Glu-Gly generation activity, whereas Vmax is 95 mol/mg/hr and Km is 21 mM as for the γ-Glu-Val generation activity. That is, if the activities are compared by using Vmax/Km as index of the activities, the ratio of γ-Glu-Val generation activity to the γ-Glu-Gly generation activity in the case of using $Mn^{2+}$ as the cofactor can be calculated to be 0.20. Further, as for the substrate specificity of GSHA derived from *Escherichia coli*, there are also other examples of measurement of the activity (Non-patent document 2). This document reported that the reaction was performed by using Glu, various kinds of amino acids, and ATP as the substrates in the presence of $Mg^{2+}$, and when the γ-Glu-Gly generation activity was taken as 100%, the γ-Glu-Val generation activity was about 52%. That is, if the activities are compared by using these relative activities, the ratio of the γ-Glu-Val generation activity to the γ-Glu-Gly generation activity can be calculated to be 0.52. Thus, it can be said that the ratio of the γ-Glu-Val generation activity to the γ-Glu-Gly generation activity of GSHA of *Escherichia coli* is about 0.15 to 0.5.

It is also known that GSHA derived from *Proteus mirabilis*, a kind of gram-negative bacteria, generates γ-glutamyl dipeptides by using $Mg^{2+}$ or $Mn^{2+}$ as a cofactor, as well as Glu, various kinds of amino acids, and ATP as substrates (Non-patent document 3). It has been reported that if the γ-Glu-Cys generation activity of GSHA derived from *Proteus mirabilis* is taken as 100%, the γ-Glu-Gly generation activity and γ-Glu-Val generation activity of the same correspond to 14.5% and 7.2%, respectively. That is, if the activities are compared on the basis of these relative activities, the ratio of γ-Glu-Val generation activity to the γ-Glu-Gly generation activity can be calculated to be 0.50.

It is also known that γ-glutamylcysteine synthetase-glutathione synthetase (γ-GCS-GS) of *Streptococcus agalactiae* generates γ-glutamyl dipeptides by using Glu, various kinds of amino acids, and ATP as the substrates in the presence of $Mg^{2+}$. As for γ-GCS-GS of *Streptococcus agalactiae*, it was reported that when the γ-Glu-Gly generation activity was taken as 100%, the γ-Glu-Val generation activity was about 21% (Non-patent document 2). That is, if the activities are compared on the basis of these relative activities, the ratio of γ-Glu-Val generation activity to the γ-Glu-Gly generation activity can be calculated to be 0.21.

Further, it was reported that culture broth of *Micrococcus glutamicus* was applied to various columns to separate peptides etc., and thereby γ-Glu-Glu, γ-Glu-Val, and γ-Glu-Leu were isolated (Non-patent document 5). However, the biosynthetic pathways of these γ-glutamyl dipeptides were not reported.

As described above, although there are some findings concerning generation of γ-Glu-Val, there has not been reported a protein having the γ-Glu-Val generation activity and showing a ratio of the γ-Glu-Val generation activity to γ-Glu-Gly generation activity larger than about 0.5.

PRIOR ART REFERENCES

Patent Documents

Patent document 1: WO2007/055388
Patent document 2: WO2007/055393
Patent document 3: WO2008/139945
Patent document 4: WO2008/139946
Patent document 5: WO2008/139947
Patent document 6: WO2009/107660
Patent document 7: WO2009/119554
Patent document 8: Japanese Patent Laid-open (Kokai) No. 08-119916
Patent document 9: WO2013/054447
Patent document 10: Japanese Patent Laid-open (Kokai) No. 2012-85637
Patent document 11: WO2013/051685

Non-Patent Documents

Non-patent document 1: Brenda S. Kelly et al., J. Biol. Chem., 277, 50-58, 2002
Non-patent document 2: Kino, K. et al., Biochem. Biophys. Res. Commun., 352, 351-359, 2007
Non-patent document 3: Kumagai, H. et al., Agric. Biol. Chem., 46, 1301-1309, 1982
Non-patent document 4: Ronald A. Vitali et al., J. Biol. Chem., 240, 2508-2511, 1965

SUMMARY OF THE INVENTION

Object to be Achieved by the Invention

Glutamate-cysteine ligase (GSHA) plays a role of generating γ-Glu-Cys, which is a precursor of glutathione, in vivo. Although GSHA may use various amino acids as a substrate besides Cys, the activity for using Val, which is a kind of branched chain amino acid, as a substrate is typically relatively low compared with that for using Cys. Therefore, when γ-Glu-Val-Gly is produced by using GSHA and glutathione synthetase (GSHB) with Glu, Val, and Gly as raw materials, there arises a problem that the yield of γ-Glu-Val-Gly is low. Therefore, an object of the present invention is to provide a protein having γ-Glu-Val generation activity (γ-Glu-Val synthetase) suitable for generating γ-Glu-Val, and a method for producing γ-Glu-Val-Gly using it.

Means for Achieving the Object

The inventors of the present invention conducted various researches in order to achieve the aforementioned object, as a result, found a protein having the γ-Glu-Val generation activity (γ-Glu-Val synthetase) and showing a high ratio of the γ-Glu-Val generation activity to the γ-Glu-Gly generation activity, and accomplished the present invention.

Thus, the present invention can be embodied, for example, as follows.

[1]
A method for producing γ-Glu-Val and/or a salt thereof, the method comprising the following step (A):
(A) a step of allowing a protein defined in (a), (b), or (c) mentioned below to act on Glu and Val to generate γ-Glu-Val:
(a) a protein comprising the amino acid sequence of SEQ ID NO: 6, 10, 16, or 22;
(b) a protein comprising the amino acid sequence of SEQ ID NO: 6, 10, 16, or 22 but including substitution, deletion, insertion, or addition of 1 to 10 amino acid residues, and having γ-glutamylvaline synthetase activity;
(c) a protein comprising an amino acid sequence showing an identity of 90% or higher to the amino acid sequence of SEQ ID NO: 6, 10, 16, or 22, and having γ-glutamylvaline synthetase activity.

[2]
A method for producing γ-Glu-Val-Gly and/or a salt thereof, the method comprising the following steps (A) and (B):
(A) a step of allowing a protein defined in (a), (b), or (c) mentioned below to act on Glu and Val to generate γ-Glu-Val; and
(B) a step of allowing glutathione synthetase to act on γ-Glu-Val generated in the step (A) and Gly to generate γ-Glu-Val-Gly:
(a) a protein comprising the amino acid sequence of SEQ ID NO: 6, 10, 16, or 22;
(b) a protein comprising the amino acid sequence of SEQ ID NO: 6, 10, 16, or 22 but including substitution, deletion, insertion, or addition of 1 to 10 amino acid residues, and having γ-glutamylvaline synthetase activity;
(c) a protein comprising an amino acid sequence showing an identity of 90% or higher to the amino acid sequence of SEQ ID NO: 6, 10, 16, or 22, and having γ-glutamylvaline synthetase activity.

[3]
A method for producing γ-Glu-Val-Gly and/or a salt thereof, the method comprising the following step (C):
(C) a step of allowing a protein defined in (a), (b), or (c) mentioned below and glutathione synthetase to act on Glu, Val, and Gly to generate γ-Glu-Val-Gly:
(a) a protein comprising the amino acid sequence of SEQ ID NO: 6, 10, 16, or 22;
(b) a protein comprising the amino acid sequence of SEQ ID NO: 6, 10, 16, or 22 but including substitution, deletion, insertion, or addition of 1 to 10 amino acid residues, and having γ-glutamylvaline synthetase activity;
(c) a protein comprising an amino acid sequence showing an identity of 90% or higher to the amino acid sequence of SEQ ID NO: 6, 10, 16, or 22, and having γ-glutamylvaline synthetase activity.

[4]
The method mentioned above, wherein the protein shows a ratio of γ-glutamylvaline synthetase activity to γ-glutamylglycine synthetase activity of 2.0 or higher.

[5]
A method for producing γ-Glu-Val-Gly and/or a salt thereof, the method comprising the following step (C):
(C) a step of allowing a protein having γ-glutamylvaline synthetase activity and showing a ratio of γ-glutamylvaline synthetase activity to γ-glutamylglycine synthetase activity of 2.0 or higher, and glutathione synthetase to act on Glu, Val, and Gly to generate γ-Glu-Val-Gly.

[6]
The method mentioned above, wherein the protein is a purified enzyme.

[7]
The method mentioned above, wherein the protein is an immobilized enzyme.

[8]
The method mentioned above, wherein the protein is a protein contained in a culture broth of a microorganism having the protein, cultured cells of the microorganism, or a processed product of the cells.

[9]
The method mentioned above, wherein the glutathione synthetase is an enzyme contained in a culture broth of a microorganism having the enzyme, cultured cells of the microorganism, or a processed product of the cells.

[10]
The method mentioned above, wherein the protein and glutathione synthetase are enzymes contained in a culture broth of a microorganism having both enzymes, cultured cells of the microorganism, or a processed product of the cells.

[11]
The method mentioned above, wherein the microorganism has been modified so that the activity of γ-glutamyl-transferase is reduced.

[12]
The method mentioned above, wherein the microorganism is *Escherichia coli*.

[13]
The method mentioned above, wherein the step or steps is/are carried out in the presence of ATP.
[14]
A protein defined in (a), (b), or (c) mentioned below:
(a) a protein comprising the amino acid sequence of SEQ ID NO: 6;
(b) a protein comprising the amino acid sequence of SEQ ID NO: 6 but including substitution, deletion, insertion, or addition of 1 to 10 amino acid residues, and having γ-glutamylvaline synthetase activity;
(c) a protein comprising an amino acid sequence showing an identity of 90% or higher to the amino acid sequence of SEQ ID NO: 6, and having γ-glutamylvaline synthetase activity.
[15]
The protein mentioned above, which shows a ratio of γ-glutamylvaline synthetase activity to γ-glutamylglycine synthetase activity of 2.0 or higher.
[16]
A protein having γ-glutamylvaline synthetase activity, which shows a ratio of γ-glutamylvaline synthetase activity to γ-glutamylglycine synthetase activity of 2.0 or higher.
[17]
A gene encoding the protein mentioned above.
[18]
A vector carrying the gene mentioned above.
[19]
A microorganism having the gene or vector mentioned above.
[20]
The microorganism mentioned above, which has been modified so that the activity of γ-glutamyltransferase is reduced.
[21]
The microorganism mentioned above, which has a gene encoding glutathione synthetase.
[22]
The microorganism mentioned above, which is *Escherichia coli*.

BRIEF DESCRIPTION OF THE DRAWING

FIGURE A diagram showing correlation of the ratio (B)/(A), which is a ratio of γ-Glu-Val synthesis activity to γ-Glu-Gly synthesis activity, and the ratio (D)/(C), which is a ratio of the total amount of γ-Glu-Val and γ-Glu-Val-Gly to the total amount of γ-Glu-Gly and γ-Glu-Gly-Gly, observed 1 hour after the start of the reaction.

MODES FOR CARRYING OUT THE INVENTION

Hereafter, the present invention will be explained in detail. In this description, amino acids are L-amino acids, unless especially indicated.
<1> γ-Glutamylvaline Synthetase (γ-Glu-Val Synthetase)

In the present invention, the term "γ-glutamylvaline synthetase (γ-Glu-Val synthetase)" refers to a protein having the activity for catalyzing the reaction of generating γ-Glu-Val, ADP, and phosphate using Glu, Val, and ATP as substrates. This activity is also referred to as "γ-glutamylvaline synthetase activity" or "γ-Glu-Val generation (synthesis) activity".

Further, in the present invention, the activity for catalyzing the reaction of generating γ-Glu-Gly, ADP, and phosphate using Glu, Gly, and ATP as substrates is also referred to as "γ-glutamylglycine synthetase activity" or "γ-Glu-Gly generation (synthesis) activity".

Further, in the present invention, the activity for catalyzing the reaction of generating γ-Glu-Cys, ADP, and phosphate using Glu, Cys, and ATP as substrates is also referred to as "γ-glutamylcysteine synthetase activity".

In the present invention, so long as γ-glutamylvaline synthetase has the γ-glutamylvaline synthetase activity, it may or may not have an activity for generating a γ-glutamyl dipeptide other than γ-glutamylvaline. That is, for example, γ-glutamylvaline synthetase may or may not have the γ-glutamylcysteine synthetase activity. Further, for example, γ-glutamylvaline synthetase may or may not have the γ-glutamylglycine synthetase activity. It is preferred that γ-glutamylvaline synthetase does not have the γ-glutamylglycine synthetase activity.

It is preferred that γ-glutamylvaline synthetase shows a high ratio of the γ-glutamylvaline synthetase activity (specific activity) to the γ-glutamylglycine synthetase activity (specific activity). The ratio of the γ-glutamylvaline synthetase activity (specific activity) to the γ-glutamylglycine synthetase activity (specific activity) of γ-glutamylvaline synthetase may be, for example, 2.0 or higher, 5.0 or higher, 10 or higher, 15 or higher, or 20 or higher. The ratio of the γ-glutamylvaline synthetase activity (specific activity) to the γ-glutamylglycine synthetase activity (specific activity) of γ-glutamylvaline synthetase may be, for example, 100 or lower, or 50 or lower.

The ratio of the specific activities can be calculated by measuring the γ-glutamylvaline synthetase activity and γ-glutamylglycine synthetase activity under the conditions described in Example 11. Specific conditions for measurement of the activities are as follows. The γ-glutamylvaline synthetase activity of γ-glutamylvaline synthetase can be measured by adding an appropriate amount of γ-glutamylvaline synthetase to a reaction mixture (100 mmol/L Tris-HCl buffer, 10 mmol/L Glu, 10 mmol/L Val, 10 mmol/L ATP, and 10 mmol/L magnesium sulfate, pH 9.0), performing the reaction at 30° C. for 30 minutes, and calculating the activity on the basis of the amount of generated γ-Glu-Val. In the present invention, the enzymatic activity for generating 1 μmol of γ-Glu-Val in 1 minute under the aforementioned conditions is defined as 1 U of the γ-glutamylvaline synthetase activity. Similarly, the γ-glutamylglycine synthetase activity of γ-glutamylvaline synthetase can be measured by adding an appropriate amount of γ-glutamylvaline synthetase to a reaction mixture (100 mmol/L Tris-HCl buffer, 10 mmol/L Glu, 10 mmol/L Gly, 10 mmol/L ATP, and 10 mmol/L magnesium sulfate, pH 9.0), performing the reaction at 30° C. for 30 minutes, and calculating the activity on the basis of the amount of generated γ-Glu-Gly. In the present invention, the enzymatic activity for generating 1 μmol of γ-Glu-Gly in 1 minute under the aforementioned conditions is defined as 1 U of the γ-glutamylglycine synthetase activity.

Also, in particular, it is expected that if γ-glutamylvaline synthetase showing an increased γ-glutamylvaline synthetase activity (specific activity) is used, γ-glutamylvaline can be efficiently produced by using Glu and Val as raw materials.

Examples of γ-glutamylvaline synthetase include, for example, γ-glutamylvaline synthetases of *Kocuria* bacteria, *Micrococcus* bacteria, and *Corynebacterium* bacteria. Examples of the *Kocuria* bacteria include *Kocuria rosea*, and *Kocuria rhizophila*. Examples of the *Micrococcus* bacteria include *Micrococcus luteus*. Examples of the *Corynebacterium* bacteria include *Corynebacterium glutamicum*.

That is, γ-glutamylvaline synthetase may be, for example, a protein derived from such bacteria as mentioned above.

The amino acid sequence of γ-glutamylvaline synthetase of *Kocuria rosea* (AJ3132), and the nucleotide sequence of the gene encoding it are shown as SEQ ID NOS: 6 and 3, respectively. The amino acid sequence of γ-glutamylvaline synthetase of the *Kocuria rhizophila* DC2201 strain (ATCC 9341), and the nucleotide sequence of the gene encoding it are shown as SEQ ID NOS: 10 and 7, respectively. The amino acid sequence of γ-glutamylvaline synthetase of the *Micrococcus luteus* NCTC2665 strain (ATCC 15307), and the nucleotide sequence of the gene encoding it are shown as SEQ ID NOS: 16 and 11, respectively. The amino acid sequence of γ-glutamylvaline synthetase of the *Corynebacterium glutamicum* K051 strain (ATCC 13032), and the nucleotide sequence of the gene encoding it are shown as SEQ ID NOS: 22 and 17, respectively. That is, γ-glutamylvaline synthetase may be, for example, a protein having the amino acid sequence of SEQ ID NO: 6, 10, 16, or 22. Further, γ-glutamylvaline synthetase may be, for example, a protein encoded by a gene having the nucleotide sequence of SEQ ID NO: 3, 7, 11, or 17. The expression of "having an (amino acid or nucleotide) sequence" includes both cases of "containing the (amino acid or nucleotide) sequence" and "consisting of the (amino acid or nucleotide) sequence".

γ-Glutamylvaline synthetase may be a variant of the γ-glutamylvaline synthetases exemplified above (for example, a protein having the amino acid sequence shown as SEQ ID NO: 6, 10, 16, or 22), so long as the original function is maintained. Similarly, the gene encoding γ-glutamylvaline synthetase (also referred to as "γ-glutamylvaline synthetase gene") may be a variant of the γ-glutamylvaline synthetase genes exemplified above (for example, a gene having the nucleotide sequence shown as SEQ ID NO: 3, 7, 11, or 17), so long as the original function is maintained. Such a variant that maintains the original function is also referred to as "conservative variant". Examples of the conservative variant include, for example, a homologue and artificially modified version of the γ-glutamylvaline synthetases exemplified above and genes encoding them.

The expression "the original function is maintained" means that a variant of the gene or protein has a function (activity or property) corresponding to the function (activity or property) of the original gene or protein. That is, the expression "the original function is maintained" means that, in the case of γ-glutamylvaline synthetase, a variant of the protein has the γ-glutamylvaline synthetase activity. Further, the expression "the original function is maintained" may also mean that, in the case of the γ-glutamylvaline synthetase gene, a variant of the gene encodes a protein that maintains the original function (namely, a protein having the γ-glutamylvaline synthetase activity).

Examples of homologues of γ-glutamylvaline synthetase include, for example, proteins obtained from a public database by BLAST search and FASTA search using any of the aforementioned amino acid sequences as a query sequence. Also, homologues of the aforementioned γ-glutamylvaline synthetase genes can be obtained by, for example, PCR using a chromosome of any of various microorganisms as the template, and oligonucleotides prepared on the basis of any of those known gene sequences as the primers.

γ-Glutamylvaline synthetase may be a protein having an amino acid sequence corresponding to any of the aforementioned amino acid sequences (for example, a protein having the amino acid sequence shown as SEQ ID NO: 6, 10, 16, or 22), but including substitution, deletion, insertion, or addition of one or several amino acid residues at one or several positions, so long as it maintains the original function. Although the number meant by the term "one or several" can differ depending on the positions of amino acid residues in the three-dimensional structure of the protein, or the types of amino acid residues, specifically, it is, for example, 1 to 50, 1 to 40, 1 to 30, preferably 1 to 20, more preferably 1 to 10, still more preferably 1 to 5, particularly preferably 1 to 3.

The aforementioned substitution, deletion, insertion, or addition of one or several amino acid residues is a conservative mutation that maintains normal function of the protein. Typical examples of the conservative mutation are conservative substitutions. The conservative substitution is a mutation wherein substitution takes place mutually among Phe, Trp, and Tyr, if the substitution site is an aromatic amino acid; among Leu, Ile, and Val, if it is a hydrophobic amino acid; between Gin and Asn, if it is a polar amino acid; among Lys, Arg, and His, if it is a basic amino acid; between Asp and Glu, if it is an acidic amino acid; and between Ser and Thr, if it is an amino acid having a hydroxyl group. Examples of substitutions considered as conservative substitutions include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gin, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Further, such substitution, deletion, insertion, addition, inversion, or the like of amino acid residues as mentioned above includes a naturally occurring mutation (mutant or variant), such as those due to a difference of individuals or species of the organism from which the protein is derived.

γ-Glutamylvaline synthetase may be a protein having an amino acid sequence showing a homology of 80% or higher, preferably 90% or higher, more preferably 95% or higher, still more preferably 97% or higher, particularly preferably 99% or higher, to the whole of any of the aforementioned amino acid sequences, so long as the original function is maintained. In this description, "homology" can mean "identity".

γ-Glutamylvaline synthetase may be a protein encoded by a DNA that hybridizes under stringent conditions with a probe that can be prepared from any of the aforementioned nucleotide sequences (for example, the nucleotide sequence shown as SEQ ID NO: 3, 7, 11, or 17), such as a sequence complementary to a part or the whole of any of the aforementioned nucleotide sequences, so long as the original function is maintained. Such a probe can be prepared by PCR using oligonucleotides produced on the basis of any of the aforementioned nucleotide sequences as primers, and a DNA fragment containing any of the aforementioned nucleotide sequences as the template. The "stringent conditions" refer to conditions under which a so-called specific hybrid is formed, and a non-specific hybrid is not formed. Examples of the stringent conditions include those under which highly homologous DNAs hybridize to each other, for example, DNAs not less than 80% homologous, preferably not less than 90% homologous, more preferably not less than 95% homologous, still more preferably not less than 97% homologous, particularly preferably not less than 99% homologous, hybridize to each other, and DNAs less homologous than the above do not hybridize to each other, or conditions of washing of typical Southern hybridization, i.e., conditions of washing once, preferably 2 or 3 times, at a salt concentration and temperature corresponding to 1×SSC, 0.1% SDS at 60° C., preferably 0.1×SSC, 0.1% SDS at 60° C., more preferably 0.1×SSC, 0.1% SDS at 68° C. Further, for example, when a DNA fragment having a length of about 300 bp is used as the probe, the washing conditions of the hybridization can be, for example, 50° C., 2×SSC, and 0.1% SDS.

Such γ-glutamylvaline synthetase as mentioned above may be, if the amino acid sequence thereof or the nucleotide sequence of the gene encoding it was known at the time of filling of this application, excluded from γ-glutamylvaline synthetase of the present invention.

γ-Glutamylvaline synthetase may be a fusion protein with another peptide. The "another peptide" is not particularly limited so long as γ-glutamylvaline synthetase has the γ-glutamylvaline synthetase activity. The "another peptide" can be selected as required depending on various conditions such as purpose of use thereof. Examples of the "another peptide" include a peptide tag, signal peptide, and recognition sequence of a protease. The "another peptide" may be bound to, for example, either one or both of the N-terminus and C-terminus of γ-glutamylvaline synthetase. As the "another peptide", one kind of peptide may be used, or two or more kinds of peptides may be used in combination.

Specific examples of the peptide tag include an His tag, FLAG tag, GST tag, Myc tag, MBP (maltose binding protein), CBP (cellulose binding protein), TRX (thioredoxin), GFP (green fluorescent protein), HRP (horseradish peroxidase), ALP (alkaline phosphatase), and Fc region of antibody. Examples of the His tag include 6×His tag. A peptide tag can be utilized for, for example, detection and purification of the expressed γ-glutamylvaline synthetase.

The signal peptide is not particularly limited, so long as it functions in a host in which γ-glutamylvaline synthetase is expressed. Examples of the signal peptide include a signal peptide that is recognized by the Sec system secretory pathway and a signal peptide recognized by the Tat system secretory pathway. Specific examples of the signal peptide that is recognized by the Tat system secretory pathway include the TorA signal sequence of *E. coli*, the SufI signal sequence of *E. coli*, the PhoD signal sequence of *Bacillus subtilis*, the LipA signal sequence of *Bacillus subtilis*, and the IMD signal sequence of *Arthrobacter globiformis* (WO2013/118544). A signal peptide can be used for, for example, secretory production of γ-glutamylvaline synthetase. If secretory production of γ-glutamylvaline synthetase is performed by using a signal peptide, the signal peptide may be cleaved at the time of the secretion, and γ-glutamylvaline synthetase not having the signal peptide may be secreted out of the cell.

Specific examples of the recognition sequence of a protease include the recognition sequence of the Factor Xa protease and the recognition sequence of the proTEV protease. The recognition sequence of a protease can be used for, for example, cleavage of the expressed γ-glutamylvaline synthetase. Specifically, for example, when γ-glutamylvaline synthetase is expressed as a fusion protein with a peptide tag, if a recognition sequence of a protease is introduced into the connection part of γ-glutamylvaline synthetase and the peptide tag, the peptide tag can be cleaved from the expressed γ-glutamylvaline synthetase by using a protease to obtain γ-glutamylvaline synthetase not having the peptide tag.

The γ-glutamylvaline synthetase gene may be one having any of the nucleotide sequences of the γ-glutamylvaline synthetase genes exemplified above and conservative variants thereof, in which arbitrary codons are replaced with equivalent codons. For example, in the γ-glutamylvaline synthetase gene, codons may be optimized according to codon frequencies observed in the host to be used. Specifically, for example, when the start codon is not ATG, the start codon can be modified to ATG.

In the present invention, a "gene" is not limited to DNA, but may include an arbitrary polynucleotide, so long as it encodes a target protein. That is, the term "γ-glutamylvaline synthetase gene" may mean an arbitrary polynucleotide encoding γ-glutamylvaline synthetase. The γ-glutamylvaline synthetase gene may be DNA, RNA, or a combination thereof. The γ-glutamylvaline synthetase gene may be single-stranded or double-stranded. The γ-glutamylvaline synthetase gene may be a single-stranded DNA or a single-stranded RNA. The γ-glutamylvaline synthetase gene may be a double-stranded DNA, a double-stranded RNA, or a hybrid strand consisting of a DNA strand and an RNA strand. The γ-glutamylvaline synthetase gene may contain both a DNA residue and an RNA residue in a single polynucleotide chain. When the γ-glutamylvaline synthetase gene contains RNA, the aforementioned descriptions concerning DNA, such as those concerning nucleotide sequences exemplified above, may be applied to RNA with appropriately changing wordings to those for RNA as required. The mode of the γ-glutamylvaline synthetase gene can be chosen according to various conditions such as use thereof.

<2> Production of γ-Glutamylvaline Synthetase

γ-Glutamylvaline synthetase can be produced by making a host having a γ-glutamylvaline synthetase gene express the γ-glutamylvaline synthetase gene. A host having a γ-glutamylvaline synthetase gene is also referred to as host having γ-glutamylvaline synthetase. γ-Glutamylvaline synthetase can also be produced by expressing a γ-glutamylvaline synthetase gene in a cell-free protein synthesis system.

The host having a γ-glutamylvaline synthetase gene may be one inherently having the γ-glutamylvaline synthetase gene, or may be one modified so as to have the γ-glutamylvaline synthetase gene.

Examples of the host inherently having a γ-glutamylvaline synthetase gene include bacteria from which such γ-glutamylvaline synthetases as mentioned above are derived, such as *Kocuria rosea* (AJ3132), *Kocuria rhizophila* DC2201 strain (ATCC 9341), *Micrococcus luteus* NCTC2665 strain (ATCC 15307), and *Corynebacterium glutamicum* K051 strain (ATCC 13032).

Examples of the host modified so as to have a γ-glutamylvaline synthetase gene include a host introduced with a γ-glutamylvaline synthetase gene.

The host to be introduced with a γ-glutamylvaline synthetase gene is not particularly limited so long as it can express a functional γ-glutamylvaline synthetase. Examples of the host include, for example, bacteria, actinomycetes, yeast, fungi, plant cells, insect cells, and animal cells. Preferred examples of the host include microorganisms such as bacteria and yeast. More preferred examples of the host include bacteria. Examples of the bacteria include gram-negative bacteria and gram-positive bacteria. Examples of the gram-negative bacteria include, for example, bacteria belonging to the family Enterobacteriaceae, such as *Escheri*-

*chia* bacteria, *Enterobacter* bacteria, and *Pantoea* bacteria. Examples of the gram-positive bacteria include *Bacillus* bacteria, and coryneform bacteria such as *Corynebacterium* bacteria. As the host, *Escherichia coli* can be especially preferably used.

A γ-glutamylvaline synthetase gene can be obtained by cloning from an organism having the γ-glutamylvaline synthetase gene. For the cloning, a nucleic acid containing the gene, such as a genomic DNA or cDNA, can be used. A γ-glutamylvaline synthetase gene can also be obtained by chemical synthesis (Gene, 60 (1), 115-127 (1987)).

Further, the obtained γ-glutamylvaline synthetase gene can be modified as required to obtain a variant thereof. Modification of a gene can be performed by a known method. For example, by the site-specific mutagenesis method, an objective mutation can be introduced into a target site of DNA. That is, for example, a coding region of a gene can be modified by the site-specific mutagenesis method so that a specific site of the encoded protein include substitution, deletion, insertion, or addition of amino acid residues. Examples of the site-specific mutagenesis method include a method using PCR (Higuchi, R., 61, in PCR Technology, Erlich, H. A. Eds., Stockton Press, 1989; Carter P., Meth., in Enzymol., 154, 382, 1987), and a method of using a phage (Kramer, W. and Frits, H. J., Meth. in Enzymol., 154, 350, 1987; Kunkel, T. A. et al., Meth. in Enzymol., 154, 367, 1987).

The method for introducing a γ-glutamylvaline synthetase gene into a host is not particularly limited. In a host, a γ-glutamylvaline synthetase gene may be harbored in such a manner that it can be expressed under control of a promoter that functions in the host. In the host, the γ-glutamylvaline synthetase gene may exist on a vector autonomously replicable out of the chromosome such as plasmid, or may be introduced into the chromosome. The host may have only one copy of a γ-glutamylvaline synthetase gene, or may have two or more copies of a γ-glutamylvaline synthetase gene. The host may have only one kind of γ-glutamylvaline synthetase gene, or may have two or more kinds of γ-glutamylvaline synthetase genes.

The promoter for expressing a γ-glutamylvaline synthetase gene is not particularly limited so long as it is a promoter that functions in the host. The "promoter that functions in a host" refers to a promoter that shows a promoter activity in the host. The promoter may be a promoter derived from the host, or a heterologous promoter. The promoter may be a native promoter of the γ-glutamylvaline synthetase gene, or may be a promoter of another gene. The promoter may be a promoter stronger than the native promoter of the γ-glutamylvaline synthetase gene. Examples of strong promoters that function in Enterobacteriaceae bacteria, such as *Escherichia coli*, include, for example, T7 promoter, trp promoter, trc promoter, lac promoter, tac promoter, tet promoter, araBAD promoter, rpoH promoter, PR promoter, and PL promoter. Examples of strong promoters that function in coryneform bacteria include the artificially modified P54-6 promoter (Appl. Microbiol. Biotechnol., 53, 674-679 (2000)), pta, aceA, aceB, adh, and amyE promoters inducible in coryneform bacteria with acetic acid, ethanol, pyruvic acid, or the like, cspB, SOD, and tuf (EF-Tu) promoters, which are potent promoters capable of providing a large expression amount in coryneform bacteria (Journal of Biotechnology, 104 (2003) 311-323; Appl. Environ. Microbiol., 2005 December; 71 (12):8587-96), as well as lac promoter, tac promoter, and trc promoter. Further, as the stronger promoter, a highly-active type of an existing promoter may also be obtained by using various reporter genes. For example, by making the -35 and -10 regions in a promoter region closer to the consensus sequence, the activity of the promoter can be enhanced (WO00/18935). Examples of highly active-type promoter include various tac-like promoters (Katashkina J I et al., Russian Federation Patent Application No. 2006134574) and pnlp8 promoter (WO2010/027045). Methods for evaluating the strength of promoters and examples of strong promoters are described in the paper of Goldstein et al. (Prokaryotic Promoters in Biotechnology, Biotechnol. Annu. Rev., 1, 105-128 (1995)), and so forth.

Also, a terminator for termination of gene transcription may be located downstream of the γ-glutamylvaline synthetase gene. The terminator is not particularly limited so long as it functions in the bacterium of the present invention. The terminator may be a terminator derived from the host, or a heterogenous terminator. The terminator may be the native terminator of the γ-glutamylvaline synthetase gene, or a terminator of another gene. Specific examples of the terminator include, for example, T7 terminator, T4 terminator, fd phage terminator, tet terminator, and trpA terminator.

A γ-glutamylvaline synthetase gene can be introduced into a host, for example, by using a vector containing the gene. A vector containing a γ-glutamylvaline synthetase gene is also referred to as expression vector or recombinant vector for a γ-glutamylvaline synthetase gene. The expression vector for a γ-glutamylvaline synthetase gene can be constructed by, for example, ligating a DNA fragment containing the γ-glutamylvaline synthetase gene with a vector that functions in the host. By transforming the host with the expression vector for a γ-glutamylvaline synthetase gene, a transformant into which the vector has been introduced is obtained, i.e. the gene can be introduced into the host. As the vector, a vector autonomously replicable in the cell of the host can be used. The vector is preferably a multi-copy vector. Further, the vector preferably has a marker such as an antibiotic resistance gene for selection of transformant. Further, the vector may have a promoter and/or terminator for expressing the introduced gene. The vector may be, for example, a vector derived from a bacterial plasmid, a vector derived from a yeast plasmid, a vector derived from a bacteriophage, cosmid, phagemid, or the like. Specific examples of vector autonomously replicable in Enterobacteriaceae bacteria such as *Escherichia coli* include, for example, pUC19, pUC18, pHSG299, pHSG399, pHSG398, pBR322, pSTV29 (all of these are available from Takara Bio), pACYC184, pMW219 (NIPPON GENE), pTrc99A (Pharmacia), pPROK series vectors (Clontech), pKK233-2 (Clontech), pET series vectors (Novagen), pQE series vectors (QIAGEN), pACYC, and the broad host spectrum vector RSF1010. Specific examples of vector autonomously replicable in coryneform bacteria include, for example, pHM1519 (Agric. Biol. Chem., 48, 2901-2903 (1984)); pAM330 (Agric. Biol. Chem., 48, 2901-2903 (1984)); plasmids obtained by improving these and having a drug resistance gene; plasmid pCRY30 described in Japanese Patent Laid-open (Kokai) No. 3-210184; plasmids pCRY21, pCRY2KE, pCRY2KX, pCRY31, pCRY3KE, and pCRY3KX described in Japanese Patent Laid-open (Kokai) No. 2-72876 and U.S. Pat. No. 5,185,262; plasmids pCRY2 and pCRY3 described in Japanese Patent Laid-open (Kokai) No. 1-191686; pAJ655, pAJ611, and pAJ1844 described in Japanese Patent Laid-open (Kokai) No. 58-192900; pCG1 described in Japanese Patent Laid-open (Kokai) No. 57-134500; pCG2 described in Japanese Patent Laid-open (Kokai) No. 58-35197; and pCG4 and pCG11 described in Japanese Patent Laid-open (Kokai) No. 57-183799. When the expression vector is constructed, for example, a γ-glutamylvaline synthetase gene having a native promoter region as it is may be incorporated into a vector, a coding region of γ-glutamylvaline synthetase ligated downstream from such a promoter as mentioned above may be incorporated into a vector, or a coding region of γ-glutamylvaline synthetase may be incorporated into a vector downstream from a promoter originally existing in the vector.

Vectors, promoters, and terminators available in various microorganisms are disclosed in detail in "Fundamental Microbiology Vol. 8, Genetic Engineering, KYORITSU SHUPPAN CO., LTD, 1987", and those can be used.

A γ-glutamylvaline synthetase gene can also be introduced into, for example, a chromosome of a host. A gene can be introduced into a chromosome by, for example, using homologous recombination (Miller, J. H., Experiments in Molecular Genetics, 1972, Cold Spring Harbor Laboratory). Examples of the gene transfer method utilizing homologous recombination include, for example, a method using a linear DNA such as Red-driven integration (Datsenko, K. A., and Wanner, B. L., Proc. Natl. Acad. Sci. USA, 97:6640-6645 (2000)), a method of using a plasmid containing a temperature sensitive replication origin, a method of using a plasmid capable of conjugative transfer, a method of using a suicide vector not having a replication origin that functions in a host, and a transduction method using a phage. Only one copy, or two or more copies of a gene may be introduced. For example, by performing homologous recombination using a sequence which is present in multiple copies on a chromosome as a target, multiple copies of a gene can be introduced into the chromosome. Examples of such a sequence which is present in multiple copies on a chromosome include repetitive DNAs, and inverted repeats located at the both ends of a transposon. Alternatively, homologous recombination may be performed by using an appropriate sequence on a chromosome such as a gene unnecessary for implementing the present invention as a target. Further, a gene can also be randomly introduced into a chromosome by using a transposon or Mini-Mu (Japanese Patent Laid-open (Kokai) No. 2-109985, U.S. Pat. No. 5,882,888, EP 805867 B1). When the gene is introduced into a chromosome, for example, a γ-glutamylvaline synthetase gene having a native promoter region as it is may be incorporated into a chromosome, a coding region for γ-glutamylvaline synthetase ligated downstream from such a promoter as mentioned above may be incorporated into a chromosome, or a coding region for γ-glutamylvaline synthetase may be incorporated into a chromosome downstream from a promoter originally contained in the chromosome.

Introduction of a gene into a chromosome can be confirmed by, for example, Southern hybridization using a probe having a sequence complementary to a part or the whole of the gene, or PCR using primers prepared on the basis of the nucleotide sequence of the gene.

The method for the transformation is not particularly limited, and conventionally known methods can be used. Examples of transformation method include, for example, a method of treating recipient cells with calcium chloride so as to increase the permeability thereof for DNA, which has been reported for the *Escherichia coli* K-12 strain (Mandel, M. and Higa, A., J. Mol. Biol., 1970, 53, 159-162), a method of preparing competent cells from cells which are in the growth phase, followed by transformation with DNA, which has been reported for *Bacillus subtilis* (Duncan, C. H., Wilson, G. A. and Young, F. E., Gene, 1977, 1:153-167), and so forth. Further, as the transformation method, there can also be used a method of making DNA-recipient cells into protoplasts or spheroplasts, which can easily take up recombinant DNA, followed by introducing a recombinant DNA into the DNA-recipient cells, which is known to be applicable to *Bacillus subtilis*, actinomycetes, and yeasts (Chang, S. and Choen, S. N., 1979, Mol. Gen. Genet., 168:111-115; Bibb, M. J., Ward, J. M. and Hopwood, O. A., 1978, Nature, 274:398-400; Hinnen, A., Hicks, J. B. and Fink, G. R., 1978, Proc. Natl. Acad. Sci. USA, 75:1929-1933). Further, as the transformation method, the electric pulse method reported for coryneform bacteria (Japanese Patent Laid-open (Kokai) No. 2-207791) can also be used.

A host inherently having a γ-glutamylvaline synthetase gene may have been modified so that the expression of the γ-glutamylvaline synthetase gene is increased. Examples of the means for increasing the expression of a γ-glutamylvaline synthetase gene include increasing the copy number of the γ-glutamylvaline synthetase gene, and improving the transcription efficiency of the γ-glutamylvaline synthetase gene. The copy number of a γ-glutamylvaline synthetase gene can be increased by introducing the γ-glutamylvaline synthetase gene into a host. Introduction of a γ-glutamylvaline synthetase gene can be performed as described above. The γ-glutamylvaline synthetase gene to be introduced may be a gene derived from the host, or heterogenous gene. The transcription efficiency of a γ-glutamylvaline synthetase gene can be improved by replacing the promoter of the γ-glutamylvaline synthetase gene with a stronger promoter. As such stronger promoter, the strong promoters mentioned above can be used.

The host having a γ-glutamylvaline synthetase gene may also have been modified so that the activity of a protein that participates in decomposition of a γ-glutamyl peptide is reduced. Examples of the protein that participates in decomposition of a γ-glutamyl peptide include γ-glutamyltransferase (GGT). By reducing the activity of GGT, decomposition of γ-Glu-Val and γ-Glu-Val-Gly can be suppressed. The activity of GGT can be reduced by such a means as disrupting the ggt gene encoding GGT. As an example, the nucleotide sequence of the ggt gene of *Escherichia coli*, and the amino acid sequence of the protein encoded by that gene are shown as SEQ ID NOS: 29 and 30, respectively.

Hereafter, the methods for reducing the activity of a protein will be explained.

The expression "the activity of a protein is reduced" means that the activity of the protein per cell is reduced as compared with that of a non-modified strain, such as a wild-type strain and parent strain. The state that "the activity of a protein is reduced" also includes a state that the activity of the protein has completely disappeared. Specifically, the expression "the activity of a protein is reduced" means that the number of molecules of the protein per cell is reduced, and/or the function of each molecule of the protein is reduced as compared with those of a non-modified strain. That is, the term "activity" in the expression "the activity of a protein is reduced" is not limited to the catalytic activity of the protein, but may also mean the transcription amount of a gene (i.e. the amount of mRNA) encoding the protein or the translation amount of the protein (i.e. the amount of the protein). The state that "the number of molecules of the protein per cell is reduced" also includes a state that the protein does not exist at all. The state that "the function of each molecule of the protein is reduced" also includes a state that the function of each protein molecule has completely disappeared. The degree of the reduction in the activity of a protein is not particularly limited, so long as the activity is reduced as compared with that of a non-modified strain. The activity of a protein may be reduced to, for example, 50% or less, 20% or less, 10% or less, 5% or less, or 0%, as compared with that of a non-modified strain.

The modification for reducing the activity of a protein is attained by, for example, reducing the expression of a gene encoding the protein. The expression "the expression of a gene is reduced" means that the expression of the gene per cell is reduced as compared with that of a non-modified strain such as a wild-type strain and parent strain. The expression "the expression of a gene is reduced" may specifically mean that the transcription amount of the gene (i.e. the amount of mRNA) is reduced, and/or the translation amount of the gene (i.e. the amount of the protein expressed from the gene) is reduced. The state that "the expression of a gene is reduced" also includes a state that the gene is not expressed at all. The state that "the expression of a gene is reduced" is also referred to as "the expression of a gene is attenuated". The expression of a gene may be reduced to, for example, 50% or less, 20% or less, 10% or less, 5% or less, or 0%, as compared with that of a non-modified strain.

The reduction in gene expression may be due to, for example, a reduction in the transcription efficiency, a reduction in the translation efficiency, or a combination of them. The expression of a gene can be reduced by modifying an expression control sequence of the gene such as promoter, Shine-Dalgarno (SD) sequence (also referred to as ribosome-binding site (RBS)), and spacer region between RBS and the start codon of the gene. When an expression control sequence is modified, preferably one or more nucleotides, more preferably two or more nucleotides, particularly preferably three or more nucleotides, of the expression control sequence are modified. Further, a part or the whole of an expression control sequence may be deleted. The expression of a gene can also be reduced by, for example, manipulating a factor responsible for expression control. Examples of the factor responsible for expression control include low molecules responsible for transcription or translation control (inducers, inhibitors, etc.), proteins responsible for transcription or translation control (transcription factors etc.), nucleic acids responsible for transcription or translation control (siRNA etc.), and so forth. Further, the expression of a gene can also be reduced by, for example, introducing a mutation that reduces the expression of the gene into the coding region of the gene. For example, the expression of a gene can be reduced by replacing a codon in the coding region of the gene with a synonymous codon used less frequently in a host. Further, for example, the gene expression may be reduced due to disruption of a gene as described later.

The modification for reducing the activity of a protein can also be attained by, for example, disrupting a gene encoding the protein. The expression "a gene is disrupted" means that a gene is modified so that a protein that can normally function is not produced. The state that "a protein that normally functions is not produced" includes a state that the protein is not produced at all from the gene, and a state that the protein of which the function (such as activity or property) per molecule is reduced or eliminated is produced from the gene.

Disruption of a gene can be attained by, for example, deleting a part or the whole of the coding region of the gene on a chromosome. Furthermore, the whole of a gene including sequences upstream and downstream from the gene on a chromosome may be deleted. The region to be deleted may be any region such as an N-terminus region, an internal region, or a C-terminus region, so long as the activity of the protein can be reduced. Deletion of a longer region can usually more surely inactivate the gene. Further, it is preferred that reading frames of the sequences upstream and downstream from the region to be deleted are not the same.

Disruption of a gene can also be attained by, for example, introducing a mutation for an amino acid substitution (missense mutation), a stop codon (nonsense mutation), a frame shift mutation which adds or deletes one or two nucleotide residues, or the like into the coding region of the gene on a chromosome (Journal of Biological Chemistry, 272:8611-8617 (1997); Proceedings of the National Academy of Sciences, USA, 95 5511-5515 (1998); Journal of Biological Chemistry, 26 116, 20833-20839 (1991)).

Disruption of a gene can also be attained by, for example, inserting another sequence into a coding region of the gene on a chromosome. Site of the insertion may be in any region of the gene, and insertion of a longer region can usually more surely inactivate the gene. It is preferred that reading frames of the sequences upstream and downstream from the insertion site are not the same. The other sequence is not particularly limited so long as a sequence that reduces or eliminates the activity of the encoded protein is chosen, and examples thereof include, for example, a marker gene such as antibiotic resistance genes, and a gene useful for production of an objective substance.

Such modification of a gene on a chromosome as described above can be attained by, for example, preparing a deficient type gene modified so that a part of the gene is deleted and thereby the gene is unable to produce a protein that normally functions, and transforming a host with a recombinant DNA containing the deficient type gene to cause homologous recombination between the deficient type gene and the wild-type gene on a chromosome and thereby substitute the deficient type gene for the wild-type gene on the chromosome. In this procedure, if a marker gene selected according to the characteristics of the host such as auxotrophy is included in the recombinant DNA, the operation becomes easier. The protein encoded by the deficient type gene has a conformation different from that of the wild-type protein, even if it is produced, and thus the function thereof is reduced or eliminated. Such gene disruption based on gene substitution utilizing homologous recombination has already been established, and there are methods of using a linear DNA such as a method called "Red driven integration" (Datsenko, K. A, and Wanner, B. L., Proc. Natl. Acad. Sci. USA, 97:6640-6645 (2000)), and a method utilizing the Red driven integration in combination with an excision system derived from A phage (Cho, E. H., Gumport, R. I., Gardner, J. F., J. Bacteriol., 184:5200-5203 (2002)) (refer to WO2005/010175), a method of using a plasmid having a temperature sensitive replication origin, a method of using a plasmid capable of conjugative transfer, a method of utilizing a suicide vector not having a replication origin that functions in a host (U.S. Pat. No. 6,303,383, Japanese Patent Laid-open (Kokai) No. 05-007491), and so forth.

Modification for reducing activity of a protein can also be attained by, for example, a mutagenesis treatment. Examples of the mutagenesis treatment include irradiation of X-ray or ultraviolet and treatment with a mutation agent such as N-methyl-N'-nitro-N-nitrosoguanidine (MNNG), ethyl methanesulfonate (EMS), and methyl methanesulfonate (MMS).

When a protein functions as a complex consisting of a plurality of subunits, a part or all of the plurality of subunits may be modified, so long as the activity of the protein is eventually reduced. That is, for example, a part or all of a plurality of genes that encode the respective subunits may be disrupted or the like. Further, when there is a plurality of isozymes of a protein, a part or all of the activities of the plurality of isozymes may be reduced, so long as the activity of the protein is eventually reduced. That is, for example, a part or all of a plurality of genes that encode the respective isozymes may be disrupted or the like.

A reduction in the activity of a protein can be confirmed by measuring the activity of the protein.

A reduction in the activity of a protein can also be confirmed by confirming a reduction in the expression of a gene encoding the protein. A reduction in the expression of a gene can be confirmed by confirming a reduction in the transcription amount of the gene or a reduction in the amount of the protein expressed from the gene.

A reduction in the transcription amount of a gene can be confirmed by comparing the amount of mRNA transcribed from the gene with that of a non-modified strain. Examples of the method for evaluating the amount of mRNA include Northern hybridization, RT-PCR, and so forth (Molecular Cloning, Cold Spring Harbor Laboratory Press, Cold Spring Harbor (USA), 2001). The amount of mRNA is preferably reduced to, for example, 50% or less, 20% or less, 10% or less, 5% or less, or 0%, of that of a non-modified strain.

A reduction in the amount of a protein can be confirmed by Western blotting using antibodies (Molecular Cloning, Cold Spring Harbor Laboratory Press, Cold Spring Harbor (USA) 2001). The amount of the protein is preferably reduced to, for example, 50% or less, 20% or less, 10% or less, 5% or less, or 0%, of that of a non-modified strain.

Disruption of a gene can be confirmed by determining nucleotide sequence of a part or the whole of the gene, restriction enzyme map, full length, or the like of the gene depending on the means used for the disruption.

By culturing a host having a γ-glutamylvaline synthetase gene, γ-glutamylvaline synthetase can be expressed. During the culture, induction of gene expression is performed, if necessary. Conditions for culture of the host and induction of gene expression may be chosen as required depending on various conditions such as type of marker, type of promoter, and type of the host. The medium used for the culture is not be particularly limited, so long as the host can proliferate in the medium and express a γ-glutamylvaline synthetase. As the medium, for example, a usual medium that contains a carbon source, nitrogen source, sulfur source, inorganic ions, and other organic components as required can be used.

Examples of the carbon source include saccharides such as glucose, fructose, sucrose, molasses, and starch hydrolysate, alcohols such as glycerol and ethanol, and organic acids such as fumaric acid, citric acid, and succinic acid.

Examples of the nitrogen source include inorganic ammonium salts such as ammonium sulfate, ammonium chloride, and ammonium phosphate, organic nitrogen such as soybean hydrolysate, ammonia gas, and aqueous ammonia.

Examples of the sulfur source include inorganic sulfur compounds, such as sulfates, sulfites, sulfides, hyposulfites, and thiosulfates.

Examples of the inorganic ions include calcium ion, magnesium ion, manganese ion, potassium ion, iron ion, and phosphoric acid ion.

Examples of the other organic components include organic trace amount nutrients. Examples of the organic trace amount nutrients include required substances such as vitamin $B_1$, yeast extract containing such substances, and so forth.

Culture temperature may be, for example, 20 to 45° C., preferably 24 to 45° C. The culture is preferably performed as aeration culture. In the aeration culture, oxygen concentration may be adjusted to 5 to 50%, preferably about 10%, with respect to the saturated concentration. pH during the culture is preferably 5 to 9. For adjusting pH, inorganic or organic acidic or alkaline substances, such as calcium carbonate, ammonia gas, and aqueous ammonia, can be used.

By performing the culture preferably for about 10 to 120 hours under such conditions as mentioned above, a culture broth containing a γ-glutamylvaline synthetase is obtained. The γ-glutamylvaline synthetase can be accumulated in, for example, microbial cells of the host. The term "microbial cell" may be appropriately read as "cell" depending on type of the host. Depending on the host to be used and design of the γ-glutamylvaline synthetase gene, it is also possible to accumulate the γ-glutamylvaline synthetase in the periplasm, or to produce the γ-glutamylvaline synthetase out of the cells by secretory production.

The γ-glutamylvaline synthetase may be used in a state that it is contained in microbial cells or the like, or may be separated and purified from microbial cells or the like to be used as a crude enzyme fraction or a purified enzyme, as required.

That is, for example, when the γ-glutamylvaline synthetase is accumulated in microbial cells of the host, by subjecting the cells to disruption, lysis, extraction, etc. as required, the γ-glutamylvaline synthetase can be collected. The microbial cells can be collected from the culture broth by centrifugation or the like. Disruption, lysis, extraction, etc. of the cells can be performed by known methods. Examples of such methods include, for example, disruption by ultrasonication, disruption in Dyno-Mill, disruption in bead mill, disruption with French press, and lysozyme treatment. These methods may be independently used, or may be used in an appropriate combination. Also, for example, when the γ-glutamylvaline synthetase is accumulated in the medium, a culture supernatant can be obtained by centrifugation or the like, and the γ-glutamylvaline synthetase can be collected from the culture supernatant.

The γ-glutamylvaline synthetase can be purified by known methods used for purification of enzymes. Examples of such methods include, for example, ammonium sulfate fractionation, ion exchange chromatography, hydrophobic chromatography, affinity chromatography, gel filtration chromatography, and isoelectric precipitation. These methods may be independently used, or may be used in an appropriate combination. The γ-glutamylvaline synthetase may be purified to a desired extent. For example, when the γ-glutamylvaline synthetase is contaminated with an ingredient that participates in decomposition of γ-glutamyl peptides, such as GGT, it is preferable to remove such an ingredient.

The purified γ-glutamylvaline synthetase can be used as the "γ-glutamylvaline synthetase" used in the methods of the present invention. The γ-glutamylvaline synthetase may be used in a free form, or may be used as an immobilized enzyme immobilized on a solid phase of resin etc.

Not only the purified γ-glutamylvaline synthetase, but also an arbitrary fraction containing a γ-glutamylvaline synthetase may be used as the "γ-glutamylvaline synthetase" in the methods of the present invention. Such a fraction containing a γ-glutamylvaline synthetase is not particularly limited, so long as it contains a γ-glutamylvaline synthetase so that the γ-glutamylvaline synthetase can act on Glu and Val. Examples of such a fraction include, for example, a culture broth of a host having a γ-glutamylvaline synthetase gene (host having a γ-glutamylvaline synthetase), microbial cells collected from such a culture broth (cultured microbial cells), processed products of such microbial cells such as disruption product of the cells, lysate of the cells, extract of the cells (cell-free extract), and immobilized cells obtained by immobilizing such cells as mentioned above on acrylamide, carrageenan, or the like, culture supernatant collected from such a culture broth, partially purified products of these (roughly purified products), and combinations of these. These fractions each may be used alone, or may be used together with a purified γ-glutamylvaline synthetase.

<3> Glutathione Synthetase and Production Thereof

"Glutathione synthetase" is generally known as an enzyme having an activity for catalyzing the reaction of generating glutathione (γ-Glu-Cys-Gly), ADP, and phosphate by using γ-Glu-Cys, Gly, and ATP as the substrates (EC 6.3.2.3). In the present invention, this activity is also referred to as "glutathione synthetase activity".

In the present invention, an activity for catalyzing the reaction of generating γ-Glu-Val-Gly, ADP, and phosphate using γ-Glu-Val, Gly, and ATP as substrates is also referred to as "γ-glutamylvalylglycine synthetase activity" or "γ-Glu-Val-Gly generation (synthesis) activity".

In the present invention, as glutathione synthetase, one having the γ-glutamylvalylglycine synthetase activity is used. That is, in the present invention, the term "glutathione synthetase" refers to a protein having the γ-glutamylvalylglycine synthetase activity.

In the present invention, so long as glutathione synthetase has the γ-glutamylvalylglycine synthetase activity, it may or may not have an activity for generating a γ-glutamyl tripeptide other than γ-glutamylvalylglycine. That is, for example, glutathione synthetase may or may not have the glutathione synthetase activity.

The γ-glutamylvalylglycine synthetase activity of glutathione synthetase can be measured by, for example, using an appropriate amount of glutathione synthetase with a reaction mixture composition of 12.5 mM γ-Glu-Val, 12.5 mM Gly, 12.5 mM ATP, 12.5 mM $MgSO_4$, 2 mM dithiothreitol, 100 mM Tris-HCl buffer (pH 8.0) at a reaction temperature of 37° C. for a reaction time of from 1 minute to 50 hours. The enzymatic activity for generating 1 μmol of γ-Glu-Val-Gly in 1 minute under the aforementioned conditions is defined as 1 U of the γ-glutamylvalylglycine synthetase activity.

Examples of glutathione synthetase include the GshB protein encoded by the gshB gene of *Escherichia coli*, and the Gsh2 protein encoded by the GSH2 gene of *Saccharomyces cerevisiae*. Examples of glutathione synthetase also include the mutant glutathione synthetase described in WO2013/054447. The nucleotide sequence of the gshB gene of the *Escherichia coli* K-12 MG1655 strain corresponds to the sequence of the positions 3,089,900 to 3,090,850 in the genome sequence registered at the NCBI database as GenBank accession NC_000913.3. The nucleotide sequence of the gshB gene of the MG1655 strain (identical to that of the *Escherichia coli* K-12 W3110 strain) is shown as SEQ ID NO: 27. The amino acid sequence of the protein encoded by this gene is shown as SEQ ID NO: 28. That is, glutathione synthetase may be, for example, a protein encoded by a gene having the nucleotide sequence shown as SEQ ID NO: 27. Glutathione synthetase may also be, for example, a protein having the amino acid sequence shown as SEQ ID NO: 28. Glutathione synthetase may also be a variant of the aforementioned glutathione synthetase, so long as it has the γ-glutamylvalylglycine synthetase activity. To such a variant, the aforementioned descriptions concerning variant of γ-glutamylvaline synthetase can be applied mutatis mutandis. Glutathione synthetase may also be a fusion protein with another peptide. To such a fusion protein, the aforementioned descriptions concerning fusion protein of γ-glutamylvaline synthetase can be applied mutatis mutandis.

Glutathione synthetase can be produced by making a host having a gene encoding glutathione synthetase (also referred to as "glutathione synthetase gene") express the glutathione synthetase gene. The host having a glutathione synthetase gene is also referred to as host having glutathione synthetase. The host having a glutathione synthetase gene may be one inherently having the glutathione synthetase gene, or one modified so as to have the glutathione synthetase gene. Examples of such a host inherently having a glutathione synthetase gene include such microorganisms as the *Escherichia coli* having the gshB gene, and *Saccharomyces cerevisiae* having the GSH2 gene mentioned above. Examples of such a host modified so as to have a glutathione synthetase gene include a host into which the glutathione synthetase gene has been introduced. Also, a host inherently having a glutathione synthetase gene may have been modified so that the expression of a glutathione synthetase gene is increased. To the modification of a host, such as introduction of a glutathione synthetase gene, the aforementioned descriptions concerning the modification of a host, such as introduction of a γ-glutamylvaline synthetase gene, can be applied mutatis mutandis. The host for expressing a glutathione synthetase gene may have been modified so that the activity of a protein that participates in decomposition of γ-glutamyl peptides, such as γ-glutamyltransferase (GGT), is reduced. Glutathione synthetase can also be produced by expressing a glutathione synthetase gene in a cell-free protein synthesis system.

To the production of glutathione synthetase using a host having the glutathione synthetase gene, the aforementioned descriptions concerning production of γ-glutamylvaline synthetase using a host having a γ-glutamylvaline synthetase gene can be applied mutatis mutandis. The produced glutathione synthetase (such as a purified glutathione synthetase and a fraction containing glutathione synthetase) can be used as "glutathione synthetase" in the methods of the present invention. Glutathione synthetase may be independently produced, or may be produced together with γ-glutamylvaline synthetase. For example, glutathione synthetase and γ-glutamylvaline synthetase can be produced together by making a host having both a glutathione synthetase gene and a γ-glutamylvaline synthetase gene express these genes.

<4> Method for Producing γ-Glutamylvalylglycine (γ-Glu-Val-Gly)

The present invention provides a method for producing γ-Glu-Val using γ-glutamylvaline synthetase, and a method for producing γ-Glu-Val-Gly using γ-glutamylvaline synthetase. These methods are also collectively referred to as the "methods of the present invention".

<4-1> Enzymatic Method

The present invention provides a method for enzymatically producing γ-Glu-Val-Gly by using γ-glutamylvaline synthetase. This method is also referred to as the "method for producing γ-Glu-Val-Gly of the present invention (enzymatic method)".

In the present invention, Glu and Val can be reacted to generate γ-Glu-Val by using a γ-glutamylvaline synthetase. That is, the present invention provides a method for producing γ-Glu-Val, which comprises (A) a step of allowing a γ-glutamylvaline synthetase to act on Glu and Val to generate γ-Glu-Val. This method is also referred to as the "method for producing γ-Glu-Val of the present invention (enzymatic method)". The generated γ-Glu-Val can be collected from the reaction mixture, as required.

Further, by using the generated γ-Glu-Val as a raw material, γ-Glu-Val-Gly can be produced. As a method for producing γ-Glu-Val-Gly by using γ-Glu-Val as a raw material, the method of using glutathione synthetase is known (Japanese Patent Laid-open (Kokai) No. 2012-85637). Specifically, γ-Glu-Val and Gly can be reacted to generate γ-Glu-Val-Gly by using glutathione synthetase. That is, an embodiment of the method for producing γ-Glu-Val-Gly of the present invention (enzymatic method) (also referred to as the "first embodiment") is a method for producing γ-Glu-Val-Gly, which comprises (A) a step of allowing γ-glutamylvaline synthetase to act on Glu and Val to generate γ-Glu-Val, and (B) a step of allowing glutathione synthetase to act on γ-Glu-Val generated in the step (A) and Gly to generate γ-Glu-Val-Gly.

In the first embodiment, the step (A) and the step (B) may be carried out separately, or may be carried out simultaneously during a partial period or the whole period of the steps. That is, for example, the step (A) and the step (B) may be started simultaneously, or the step (B) may be started while the step (A) is in progress or after the step (A) is completed. The step (A) and the step (B) can be simultaneously started by making γ-glutamylvaline synthetase, glutathione synthetase, Glu, Val, and Gly coexist in a reaction system at the time of the start of the reaction. Alternatively, the step (A) can be started under the conditions that glutathione synthetase and/or Gly does not coexist in the reaction system, and the step (B) can be started by making glutathione synthetase and/or Gly coexist in the reaction system while the step (A) is in progress or after the step (A) is completed. Further, γ-Glu-Val generated in the step (A) may be collected, and the step (B) may be carried out by using the collected γ-Glu-Val. γ-Glu-Val may be subjected to such a treatment as purification, dilution, concentration, drying, and dissolution, as required, and then used for the step (B).

The step (A) of the method for producing γ-Glu-Val of the present invention (enzymatic method) can be carried out, for example, in the same manner as that for carrying out the step (A) of the first embodiment alone.

Also, in the present invention, Glu, Val, and Gly can be reacted to generate γ-Glu-Val-Gly by using γ-glutamylvaline synthetase and glutathione synthetase. That is, another embodiment of the method for producing γ-Glu-Val-Gly of the present invention (enzymatic method) (it is also referred to as the "second embodiment") is a method for producing γ-Glu-Val-Gly, which comprises (C) a step of allowing γ-glutamylvaline synthetase and glutathione synthetase to act on Glu, Val, and Gly to generate γ-Glu-Val-Gly. In the second embodiment, by making γ-glutamylvaline synthetase, glutathione synthetase, Glu, Val, and Gly coexist in a reaction system, γ-glutamylvaline synthetase and glutathione synthetase can be made to act on all of Glu, Val, and Gly to produce γ-Glu-Val-Gly.

In the methods of the present invention, γ-glutamylvaline synthetase and glutathione synthetase are also collectively referred to as "enzymes". Glu, Val, and Gly are also collectively referred to as "amino acids". γ-Glu-Val and γ-Glu-Val-Gly are also collectively referred to as "peptides". Glu, Val, Gly, and γ-Glu-Val are also collectively referred to as "substrates". The "substrates" may further include ATP, unless otherwise stated. A reaction of an enzyme and a substrate corresponding to the enzyme is also referred to as "enzymatic reaction".

The mode of the enzymes used for the methods of the present invention is as described above. That is, as each enzyme, for example, a purified enzyme, an arbitrary fraction containing the enzyme, or a combination of these can be used. As each enzyme, one kind of enzyme may be used, or two or more kinds of enzymes may be used in combination.

As each of the amino acids, a commercial product may be used, or one appropriately prepared and obtained may be used. The methods for producing an amino acid are not particularly limited, and, for example, known methods can be used. An amino acid can be produced by, for example, chemical synthesis, enzymatic reaction, or a combination of them. An amino acid can be produced by, for example, culturing a microorganism having an ability to produce the amino acid, and collecting the amino acid from culture. As a microorganism having an ability to produce an amino acid, for example, such amino acid-producing bacteria as described later can be used. An amino acid can also be produced by, for example, collecting the amino acid from agricultural, aquatic, and livestock products containing the amino acid. As each of the amino acids, a purified product purified to a desired extent may be used, or a material containing the amino acid may be used. Such a material containing an amino acid is not particularly limited so long as it contains an amino acid in such a manner that an enzyme can act on the amino acid. Specific examples of the material containing an amino acid include, for example, a culture broth obtained by culturing a microorganism having an ability to produce the amino acid, culture supernatant separated from the culture broth, cells separated from the culture broth, and processed products thereof such as concentrates (concentrated liquids) thereof and concentrated and dried products thereof.

In the methods of the present invention, the amino acids and peptides each may be a free compound, salt thereof, or mixture of them, unless otherwise stated. That is, the term "amino acid" may mean amino acid in the form of free compound, salt thereof, or mixture of them, unless otherwise stated. The term "peptide" may mean peptide in the form of free compound, salt thereof, or mixture of them, unless otherwise stated. The salt is not particularly limited so long as it is a chemically acceptable salt. When the produced γ-Glu-Val-Gly is used for oral use (for example, use as an additive for foods and drinks), the salt of γ-Glu-Val-Gly is not particularly limited so long as it is a chemically acceptable edible salt. Specific examples of the "chemically acceptable edible salt" include, for acidic groups such as carboxyl group, for example, ammonium salts, salts with alkali metals such as sodium and potassium, salts with alkaline earth metals such as calcium and magnesium, aluminum salts, zinc salts, salts with organic amines such as triethylamine, ethanolamine, morpholine, pyrrolidine, piperidine, piperazine, and dicyclohexylamine, and salts with basic amino acids such as arginine and lysine. Specific examples of the "chemically acceptable edible salt" include, for basic groups, for example, salts with inorganic acids such as hydrochloric acid, sulfuric acid, phosphoric acid, nitric acid, and hydrobromic acid, salts with organic carboxylic acids such as acetic acid, citric acid, benzoic acid, maleic acid, fumaric acid, tartaric acid, succinic acid, tannic acid, butyric acid, hibenzic acid, pamoic acid, enanthic acid, decanoic acid, teoclic acid, salicylic acid, lactic acid, oxalic acid, mandelic acid, and malic acid, and salts with organic sulfonic acid such as methanesulfonic acid, benzenesulfonic acid, and p-toluenesulfonic acid. As the salt, one kind of salt may be used, or two or more kinds of salts may be used in combination.

The enzymatic reaction may be performed by the batch method or the column method. When the batch method is used, the enzymatic reaction can be performed by mixing the enzyme and the substrates in a reaction mixture contained in a reaction vessel. The enzymatic reaction may be performed in a stationary state, or with stirring. When the column method is used, the enzymatic reaction can be performed by passing a reaction mixture containing the substrates thorough a column filled with immobilized cells or immobilized enzyme. As the reaction mixture, water, buffer, or the like containing required ingredients can be used. The reaction mixture may contain, for example, the enzyme(s), substrates, ATP, and divalent metal ions. Combination of the ingredients used for the enzymatic reaction can be appropriately chosen according to type and implementation scheme of the step to be performed, such as whether two or more of steps are simultaneously carried out or not.

Both γ-glutamylvaline synthetase and glutathione synthetase use ATP for the enzymatic reaction. Therefore, ATP is supplied to the reaction system as required. That is, the reaction system (reaction mixture) may contain ATP. All of the aforementioned steps (A) to (C) can be carried out in the presence of ATP. The method for supplying ATP is not particularly limited so long as ATP can be used for the enzymatic reaction. ATP can be added to the reaction mixture in an arbitrary form, for example, in the form of powder or aqueous solution. ATP may also be supplied to the reaction system by, for example, a method for generating or regenerating ATP. As the method for generating or regenerating ATP, there are known the method of supplying ATP from a carbon source by using a *Corynebacterium* bacterium (Hori, H. et al., Appl. Microbiol. Biotechnol., 48(6):693-698 (1997)), the method of regenerating ATP by using yeast cells and glucose (Yamamoto, S et al., Biosci. Biotechnol. Biochem., 69(4):784-789 (2005)), the method of regenerating ATP using phosphoenolpyruvic acid and pyruvate kinase (C. Aug'e and Ch. Gautheron, Tetrahedron Lett., 29:789-790 (1988)), the method of regenerating ATP by using polyphosphoric acid and polyphosphate kinase (Murata, K. et al., Agric. Biol. Chem., 52(6):1471-1477 (1988)), and so forth.

Also, for example, γ-glutamylvaline synthetase typically requires a divalent metal ion for the enzymatic reaction. Therefore, the reaction system (reaction mixture) may contain a divalent metal ion. All of the steps (A) to (C) can be carried out in the presence of a divalent metal ion. Preferred examples of the divalent metal ion include $Mg^{2+}$ and $Mn^{2+}$. The concentration of the divalent metal ion may be, for example, 1 to 200 mM.

Reaction conditions (pH of the reaction mixture, reaction temperature, reaction time, concentrations of various ingredients such as substrates and enzyme, etc.) are not particularly limited so long as γ-Glu-Val-Gly is generated.

pH of the reaction mixture may be, for example, usually 6.0 to 10.0, preferably 6.5 to 9.0.

The reaction temperature may be, for example, usually 15 to 50° C., preferably 15 to 45° C., more preferably 20 to 40° C.

The reaction time may be, for example, 5 minutes to 200 hours for each of the steps (A) and (B) of the first embodiment. The reaction time may be, for example, 5 minutes to 200 hours for the step (C) of the second embodiment. Flow rate of the reaction mixture may be, for example, such a rate that the reaction time should be within the range of the reaction time exemplified above.

The concentration of each of the substrates in the reaction mixture may be, for example, usually 0.1 to 2000 mM, preferably 1 to 2000 mM, more preferably 10 to 1000 mM.

Molar ratio of the substrates in the reaction mixture for the step (A) of the first embodiment may be set so that, for example, usually, Glu:Val:ATP is 1:1:1, and ratio of an arbitrary substrate may be changed within the range of 0.1 to 10. That is, for example, Glu:Val:ATP may be 0.1 to 10:0.1 to 10:0.1 to 10. As for the step (B) of the first embodiment, the molar ratio of the substrates in the reaction mixture may be set so that, for example, usually, γ-Glu-Val:Gly:ATP is 1:1:1, and ratio of an arbitrary substrate may be changed within the range of 0.1 to 10. That is, for example, γ-Glu-Val:Gly:ATP may be 0.1 to 10:0.1 to 10:0.1 to 10. Molar ratio of the substrates in the reaction mixture for the step (C) of the second embodiment may be set so that, for example, usually, Glu:Val:Gly:ATP is 1:1:1:2, ratio of an arbitrary substrate may be changed within the range of 0.1 to 10, and ratio of ATP may be changed within the range of 0.2 to 20. That is, for example, Glu:Val:Gly:ATP may be 0.1 to 10:0.1 to 10:0.1 to 10:0.2 to 20. When the step (A) and the step (B) are simultaneously carried out in the first embodiment, molar ratio of the substrates in the first embodiment may be determined with reference to the molar ratio of the substrates for the second embodiment, as required.

The amount of the enzyme to be used can be set on the basis of, for example, enzymatic activity. The amount of γ-glutamylvaline synthetase to be used may be, for example, usually 0.01 to 1000 U, preferably 0.1 to 500 U, more preferably 0.1 to 100 U, in terms of the γ-Glu-Val generation activity, with respect to 1 mmol of the total amount of Glu and Val. As for the step (B) of the first embodiment, the amount of glutathione synthetase to be used may be, for example, usually 0.01 to 1000 U, preferably 0.1 to 500 U, more preferably 0.1 to 100 U, in terms of the γ-Glu-Val-Gly generation activity, with respect to 1 mmol of the total amount of γ-Glu-Val and Gly. As for the step (C) of the second embodiment, the amount of glutathione synthetase to be used may be, for example, usually 0.01 to 1000 U, preferably 0.1 to 500 U, more preferably 0.1 to 100 U, in terms of the γ-Glu-Val-Gly generation activity, with respect to 1 mmol of the total amount of a half of the amount of Glu, a half of the amount of Val, and the whole amount of Gly. When the step (A) and the step (B) are simultaneously carried out in the first embodiment, the amount of glutathione synthetase to be used in the first embodiment may be determined with reference to the amount of glutathione synthetase to be used in the second embodiment, as required.

In any of the embodiments, in the course of the enzymatic reaction, the substrates, enzymes, and/or other ingredients may be additionally added to the reaction system independently or in an arbitrary combination. These ingredients may be added at one time, or two or more times, or they may be continuously added. The reaction conditions may be constant from the start to the end of the enzymatic reaction, or may change in the course of the enzymatic reaction. The expression "the reaction conditions change in the course of the enzymatic reaction" is not limited to cases where the reaction conditions temporally change, but also includes cases where the reaction conditions spatially change. The expression that "the reaction conditions spatially change" means that, for example, when the enzymatic reaction is performed by the column method, the reaction conditions such as reaction temperature and enzyme concentration are different depending on the position on the flowing pathway.

By carrying out the enzymatic reaction as described above, a reaction mixture containing γ-Glu-Val-Gly can be obtained. Generation of γ-Glu-Val-Gly can be confirmed by a known technique used for detection or identification of a compound. Examples of such a technique include, for example, HPLC, LC/MS, GC/MS, and NMR. These techniques may be independently used, or may be used in an appropriate combination. γ-Glu-Val-Gly can be collected from the reaction mixture as required. γ-Glu-Val-Gly can be collected by a known technique used for separation and purification of a compound. Examples of such a technique include, for example, various chromatography techniques such as ion exchange chromatography, reverse phase high performance liquid chromatography, and affinity chromatography, as well as crystallization and recrystallization from a solution. These techniques may be independently used, or may be used in an appropriate combination. The collected γ-Glu-Val-Gly may contain ingredients other than γ-Glu-Val-Gly, such as ingredients used for the production of γ-Glu-Val-Gly and moisture. γ-Glu-Val-Gly may be purified to a desired extent. γ-Glu-Val-Gly may be purified to a purity of, for example, 30% (w/w) or higher, 50% (w/w) or higher, 70% (w/w) or higher, 80% (w/w) or higher, 90% (w/w) or higher, or 95% (w/w) or higher. γ-Glu-Val can be collected in a manner similar to that for the collection of γ-Glu-Val-Gly.

<4-2> Fermentative Method

The present invention provides a method for producing γ-Glu-Val-Gly by fermentation using γ-glutamylvaline synthetase. This method is also referred to as the "method for producing γ-Glu-Val-Gly of the present invention (fermentative method)".

In the present invention, γ-Glu-Val can be produced from Glu and Val by fermentation by using a microorganism having γ-glutamylvaline synthetase. That is, the present invention provides a method for producing γ-Glu-Val, which comprises (A) a step of generating γ-Glu-Val from Glu and Val by culturing a microorganism having γ-glutamylvaline synthetase in a medium. This method is also referred to as the "method for producing γ-Glu-Val of the present invention (fermentative method)". The generated γ-Glu-Val can be collected from the culture as required.

Further, γ-Glu-Val-Gly can be produced by fermentation from γ-Glu-Val and Gly by using a microorganism having glutathione synthetase. That is, an embodiment of the method for producing γ-Glu-Val-Gly of the present invention (fermentative method) (also referred to as "third embodiment") is a method for producing γ-Glu-Val-Gly, which comprises (A) a step of generating γ-Glu-Val from Glu and Val by culturing a microorganism having γ-glutamylvaline synthetase in a medium, and (B) a step of generating γ-Glu-Val-Gly from γ-Glu-Val generated in the step (A) and Gly by culturing a microorganism having glutathione synthetase in a medium.

In the third embodiment, the step (A) and the step (B) may be carried out separately, or may be carried simultaneously during a partial period or the whole period of the steps. That is, for example, the step (A) and the step (B) may be started simultaneously, or the step (B) may be started while the step (A) is in progress or after the step (A) is completed. In the third embodiment, the step (A) and the step (B) may be carried out by using a microorganism having γ-glutamylvaline synthetase and another microorganism having glutathione synthetase, or may be carried out by using a single kind of microorganism having both γ-glutamylvaline synthetase and glutathione synthetase. For example, if a microorganism having both γ-glutamylvaline synthetase and glutathione synthetase is used, and it is cultured in a state that Glu, Val, and Gly are available, the step (A) and the step (B) can be simultaneously carried out. Further, γ-Glu-Val generated in the step (A) may be collected, and added to a medium to carry out the step (B). γ-Glu-Val may be subjected to such a treatment as purification, dilution, concentration, drying, and dissolution, as required, and then used for the step (B).

The step (A) of the method for producing γ-Glu-Val of the present invention (fermentative method) can be carried out, for example, in the same manner as that for carrying out the step (A) of the third embodiment alone.

Also, in the present invention, γ-Glu-Val-Gly can be produced by fermentation from Glu, Val, and Gly by using a microorganism having both γ-glutamylvaline synthetase and glutathione synthetase. That is, another embodiment of the method for producing γ-Glu-Val-Gly of the present invention (fermentative method) (also referred to as "fourth embodiment") is a method for producing γ-Glu-Val-Gly, which comprises (C) a step of generating γ-Glu-Val-Gly from Glu, Val, and Gly by culturing a microorganism having γ-glutamylvaline synthetase and glutathione synthetase in a medium.

In the fermentative method, such terms as enzymes, amino acids, peptides, substrates, and enzymatic reaction are used in the same meanings as those used for the enzymatic method. A microorganism having γ-glutamylvaline synthetase, microorganism having glutathione synthetase, and microorganism having γ-glutamylvaline synthetase and glutathione synthetase are also generically referred to as "microorganisms".

The method for supplying amino acids used as the substrates is not particularly limited so long as the amino acids can be used for the enzymatic reaction. For example, the amino acids each may be biosynthesized by a microorganism used in the corresponding step, may be added to the medium, or may be supplied by a combination of the foregoing means. That is, for example, all of Glu, Val, and Gly may be biosynthesized by a microorganism, or all of Glu, Val, and Gly may be added to the medium. Alternatively, for example, one or two kinds of amino acids among Glu, Val, and Gly may be biosynthesized by a microorganism, and the other amino acid(s) may be added to the medium. All of Glu, Val, and Gly may also be biosynthesized by a microorganism, and added to the medium.

That is, an embodiment of the method for producing γ-Glu-Val of the present invention (fermentative method) may be, for example, a method for producing γ-Glu-Val, which comprises (A1) a step of generating γ-Glu-Val by culturing a microorganism having γ-glutamylvaline synthetase in a medium containing Glu and Val, or a method for producing γ-Glu-Val, which comprises (A2) a step of generating γ-Glu-Val by culturing a microorganism having γ-glutamylvaline synthetase and having an ability to produce Glu and Val in a medium.

Also, an embodiment of the third embodiment may be, for example, a method for producing γ-Glu-Val-Gly, which comprises the step of (A1) or (A2), and the step of (B1) or (B2):

(A1) a step of generating γ-Glu-Val by culturing a microorganism having γ-glutamylvaline synthetase in a medium containing Glu and Val;

(A2) a step of generating γ-Glu-Val by culturing a microorganism having γ-glutamylvaline synthetase and having an ability to produce Glu and Val in a medium;

(B1) a step of generating γ-Glu-Val-Gly by culturing a microorganism having glutathione synthetase in a medium containing γ-Glu-Val generated in the step (A1) or (A2), and Gly;

(B2) a step of generating γ-Glu-Val-Gly by culturing a microorganism having glutathione synthetase and having an ability to produce Gly in a medium containing γ-Glu-Val generated in the step (A1) or (A2).

Further, an embodiment of the fourth embodiment may be, for example, a method for producing γ-Glu-Val-Gly, which comprises (C1) a step of generating γ-Glu-Val-Gly by culturing a microorganism having γ-glutamylvaline synthetase and glutathione synthetase in a medium containing Glu, Val, and Gly, or a method for producing γ-Glu-Val-Gly, which comprises (C2) a step of generating γ-Glu-Val-Gly by culturing a microorganism having γ-glutamylvaline synthetase and glutathione synthetase and having an ability to produce Glu, Val, and Gly in a medium.

As the microorganism having γ-glutamylvaline synthetase, such a microorganism having a γ-glutamylvaline synthetase gene as mentioned above can be used as it is, or after modification as required. As the microorganism having glutathione synthetase, such a microorganism having a glutathione synthetase gene as mentioned above can be used as it is, or after modification as required. As the microorganism having γ-glutamylvaline synthetase and glutathione synthetase, such a microorganism having a γ-glutamylvaline synthetase gene and a glutathione synthetase gene as mentioned above can be used as it is, or after modification as required.

The microorganism having an ability to produce an amino acid may be one inherently having the ability to produce an amino acid, or may be one modified to have the ability to produce an amino acid. A microorganism having an ability to produce an amino acid can be obtained by imparting an amino acid-producing ability to a microorganism, or by enhancing an amino acid-producing ability of a microorganism. Either the impartation or enhancement of an enzyme-producing ability, such as introduction of a γ-glutamylvaline synthetase gene and/or a glutathione synthetase gene, or impartation or enhancement of an amino acid-producing ability may be carried out first. That is, a microorganism having γ-glutamylvaline synthetase and/or glutathione synthetase and having an ability to produce an amino acid may be obtained by modifying a microorganism having γ-glutamylvaline synthetase and/or glutathione synthetase to have an amino acid-producing ability, or may be obtained by modifying a microorganism having an amino acid-producing ability to have γ-glutamylvaline synthetase and/or glutathione synthetase. An L-amino acid-producing ability can be imparted or enhanced by methods conventionally employed in the breeding of amino acid-producing strains of coryneform bacteria, Escherichia bacteria, and so forth (see "Amino Acid Fermentation", Gakkai Shuppan Center Ltd., 1st Edition, published May 30, 1986, pp.77-100). Such methods include, for example, acquiring an auxotrophic mutant strain, an L-amino acid analogue-resistant strain, or a metabolic regulation mutant strain, and constructing a recombinant strain in which the activity of an L-amino acid biosynthesis system enzyme is enhanced. An L-amino acid-producing ability can also be imparted or enhanced by reducing the activity of an enzyme that catalyzes a reaction branching away from biosynthetic pathway of a target L-amino acid to generate a compound other than the target L-amino acid.

Examples of L-glutamic acid-producing bacteria include a recombinant strain obtained by introducing the mviN gene having V197M mutation into an odhA-deficient strain obtained from the Corynebacterium glutamicum (Brevibacterium lactofermentum) ATCC 13869 strain (Japanese Patent Laid-open (Kokai) No. 2010-161970), the Pantoea agglomerans AJ13355 strain introduced with the gltA (citrate synthase) gene derived from Brevibacterium lactofermentum (Japanese Patent No. 4285582), an Escherichia bacterium having glutamine synthetase in which the tyrosine residue at position 397 is replaced with another amino acid residue (U.S. Patent Published Application No. 2003/0148474), and so forth. Examples of L-valine-producing bacteria include the Escherichia coli VL1970 strain (U.S. Pat. No. 5,658,766), an Escherichia bacterium having a mutation for requiring lipoic acid for growth thereof and/or a mutation for lacking $H^+$-ATPase, an Escherichia bacterium that is, in addition to these characteristics, intracellularly introduced with a DNA fragment containing the ilvGMEDA operon that expresses at least the ilvG, ilvM, ilvE, and ilvD genes, but does not express the threonine deaminase activity (WO96/06926), and so forth. That is, for example, by introducing any of these modifications into a microorganism, an amino acid-producing ability can be imparted or enhanced.

The microorganism may also have been modified so that the ability to uptake an amino acid added to the medium is improved. The microorganism may also have been modified so that the ability to excrete the generated γ-Glu-Val out of the cell is improved, or it may have been modified so that the ability to uptake γ-Glu-Val added to the medium is improved, depending on the scheme of use of the microorganism. The microorganism may also have been modified so that the ability to excrete the generated γ-Glu-Val-Gly out of the cell is improved.

Culture conditions are not particularly limited, so long as the microorganism can proliferate, and γ-Glu-Val-Gly is generated. For the culture conditions, the descriptions concerning the culture conditions for the method for producing γ-glutamylvaline synthetase mentioned above can be referred to.

Both γ-glutamylvaline synthetase and glutathione synthetase use ATP for the enzymatic reaction. Therefore, ATP is supplied to the reaction system as required. That is, the reaction system may contain ATP. All of the aforementioned steps (A) to (C) can be carried out in the presence of ATP. The method for supplying ATP is not particularly limited so long as ATP can be used for the enzymatic reaction. ATP may be, for example, generated by a microorganism used in each step, or supplied to the reaction system by such a method for generating or regenerating ATP as mentioned above. For supplying ATP, for example, there can be preferably used a co-culture system such as those realized by a method of making a microorganism of which ATP regenerating system based on the usual energy metabolism is enhanced, or a microorganism having an ability to regenerate ATP by the action of polyphosphate kinase coexist in the culture medium (Japanese Patent Publication (Kokoku) Nos. 7-16431 and 6-69386).

Also, for example, γ-glutamylvaline synthetase typically requires a divalent metal ion for the enzymatic reaction. Therefore, the reaction system may contain a divalent metal ion. All of the steps (A) to (C) mentioned above can be carried out in the presence of a divalent metal ion.

When a medium containing an amino acid is used, the amino acid may be contained in the medium from the start of the culture, or may be added to the medium at an arbitrary time during the culture. Although the time of the addition can be changed as required according to various conditions such as culture time, the amino acid may be added, for example, preferably 0 to 50 hours, more preferably 0.1 to 24 hours, particularly preferably 0.5 to 6 hours, before the end of the culture. The amino acid may be added at one time, or two or more times, or it may be continuously added. The concentration of each of the amino acids in the medium may be, for example, usually 0.1 to 2000 mM, preferably 1 to 2000 mM, more preferably 10 to 1000 mM. As for molar ratio of substrates in the medium, the descriptions concerning the molar ratio of substrates in the reaction mixture for the enzymatic method may be applied mutatis mutandis.

By performing culture as described above, a culture broth containing γ-Glu-Val-Gly can be obtained. Generation of γ-Glu-Val-Gly can be confirmed by a known technique used for detection or identification of a compound as described above. γ-Glu-Val-Gly can be collected from the culture broth as required. γ-Glu-Val-Gly can be collected by a known technique used for separation or purification of a compound as described above. When γ-Glu-Val-Gly is accumulated in the cells, for example, the cells can be disrupted by ultrasonication or the like, and γ-Glu-Val-Gly can be collected by the ion-exchange resin method or the like from supernatant obtained by removing the cells by centrifugation.

When the microorganism is yeast, and γ-Glu-Val-Gly is accumulated in the cells thereof, this yeast can be used for, for example, production of yeast extract containing γ-Glu-Val-Gly. That is, the present invention provides a method for producing yeast extract containing γ-Glu-Val-Gly, which comprises preparing yeast extract by using the yeast as a raw material. The yeast extract can be prepared from the yeast in the same manner as usual production of yeast extract. The yeast extract may be one obtained by hot water extraction of the yeast cells followed by treatment of the resulting extract, or one obtained by digestion of the yeast cells followed by treatment of the digested product. The obtained yeast extract may be concentrated, or may be dried to make it in the form of powder, as required.

EXAMPLES

Hereafter, the present invention will be more specifically explained with reference to examples.

Example 1 Detection of γ-Glu-Val Synthesis Activity in Kocuria Rosea (AJ3132) Cell-Free Extract (1) Preparation of Cell-Free Extract For the culture of Kocuria rosea (AJ3132), a medium 1 (0.5% (w/v) glucose, 1% (w/v) yeast extract, 1% (w/v) polypeptone, 0.5% (w/v) NaCl (pH 7.0)) was used. Kocuria rosea (AJ3132) was cultured overnight at 30° C. on the medium 1 containing 1.5% (w/v) agar. The obtained cells were inoculated into 18 ml of the medium 1, the medium was put into test tubes in a volume of 3 ml each, and culture was performed overnight at 30° C. with shaking by reciprocal movement of 120 times/minute. The cells were collected by centrifugation (12,000 g, 5 minutes), washed with physiological saline, and made into 4 ml of a cell suspension by using physiological saline. The cells in the cell suspension was disrupted by using Multibeads Shocker_Model MB701CAJ (S) (Yasui Kikai, bead diameter 0.1 mm, 2,700 rpm, ON/OFF=1 minute/1 minute, 6 minutes in total), and then the disrupted product was centrifuged (12,000 g, 10 minutes). The centrifugation supernatant was subjected to ultrafiltration by using Amicon Ultra Filter Unit 3,000 NMWL (Merck Millipore). The filter-non-permeable liquid was collected, and diluted with physiological saline to a total volume of 4 ml to prepare a cell-free extract.

(2) Detection of γ-Glu-Val Synthesis Activity

A 0.08 ml aliquot of the cell-free extract was added to 0.12 ml of a reaction mixture 1 (100 mmol/L Tris-HCl buffer, 50 mmol/L Glu, 50 mmol/L Val, 10 mmol/L adenosine triphosphate (ATP), 10 mmol/L magnesium sulfate, pH 8.5) to start the enzymatic reaction in a total volume of 0.2 ml. As a control, the enzymatic reaction was performed under the condition that physiological saline was added to the reaction mixture 1 instead of the cell-free extract. The reaction was performed at 30° C. for 17 hours, and after completion of the reaction, γ-Glu-Val was quantified by HPLC.

The quantification conditions for γ-Glu-Val were as follows. Synergi 4μ Hydro-RP 80A produced by Phenomenex (particle size 4 microns, inner diameter 4.6 mm, length 250 mm) was used as the column. As the eluent, a solution A (50 mM sodium dihydrogenphosphate (pH 2.5, adjusted with phosphoric acid)) and a solution B (1:1 (v/v) mixture of the solution A and acetonitrile) were used. The column temperature was 40° C., and UV detection wavelength was 210 nm. The gradient of the eluent was constituted with 0 to 5% of the solution B for the period of 0 to 5 minutes, 5% of the solution B for 5 to 15 minutes, 5 to 80% of the solution B for 15 to 30 minutes, 80 to 0% of the solution B for 30 to 30.1 minutes, and 0% of the solution B for 30.1 to 50 minutes.

The results are shown in Table 1. Generation of γ-Glu-Val with the cell-free extract of Kocuria rosea (AJ3132) was observed. That is, γ-Glu-Val synthesis activity was detected in the cell-free extract of Kocuria rosea (AJ3132).

TABLE 1

|  | γ-Glu-Val (mmol/L) |
| --- | --- |
| Control | 0.000 |
| Kocuria rosea cell-free extract | 0.429 |

Example 2 Purification of γ-Glu-Val Synthetase Derived from Kocuria Rosea (AJ3132)

In Examples 2, the γ-Glu-Val synthesis activity was measured in the same manner as that of Example 1 by adding an appropriate amount of an enzyme solution (cell-free extract or active fraction) to the reaction mixture 1 described in Example 1 (the same shall apply to the following examples, unless otherwise stated). In Example 2, the enzymatic activity for generating 1 μmol of γ-Glu-Val in 1 minute under these conditions was defined as 1 U of the γ-Glu-Val synthesis activity.

(1) Preparation of Cell-Free Extract

Kocuria rosea (AJ3132) was cultured overnight at 30° C. on the medium 1 containing 1.5% (w/v) agar. The obtained cells were inoculated into 4 L of the medium 1, the medium was put into 500 ml-volume Sakaguchi flasks in a volume of 100 ml each, and culture was performed at 30° C. for 16 hours with shaking by reciprocal movement of 110 times/minute. The cells were collected by centrifugation (12,000 g, 5 minutes), washed with a 20 mM potassium phosphate buffer (pH 6.0), and made into 600 ml of a cell suspension by using the same buffer. The cells in the cell suspension were disrupted by using Multibeads Shocker (Yasui Kikai), the disrupted product was centrifuged (400 g, 1 minute), and the obtained supernatant was further centrifuged (29,100 g, 20 minutes). The obtained supernatant was subjected to ultracentrifugation (274,000 g, 30 minutes), and 410 ml of the supernatant was collected as cell-free extract (total protein amount 1665 mg, total activity (total γ-Glu-Val synthesis activity) 6.9 U).

(2) Anion Exchange Chromatography

The cell-free extract obtained in (1) mentioned above was applied to a HiLoad 26/10 Q Sepharose High Performance column (GE Healthcare) equilibrated beforehand with a 20 mM potassium phosphate buffer (pH 6.0), and the enzyme was eluted with a linear concentration gradient of 0 to 1 M sodium chloride. Among the eluted fractions, fractions that showed the γ-Glu-Val synthesis activity were collected as an active fraction (total protein amount 128 mg, total activity 3.6 U).

(3) Hydrophobic Interaction Chromatography

The active fraction obtained in (2) mentioned above was mixed with the same volume of a 20 mM potassium phosphate buffer (pH 6.0) containing 2.4 M ammonium sulfate, and the mixture was gently stirred at 4° C. for 3 hours, and then centrifuged (12,000 g, 5 minutes) to obtain a supernatant (total protein amount 88 mg, total activity 3.5 U). The obtained supernatant was applied to a HiTrap Phenyl High Performance 5 ml column (GE Healthcare) equilibrated beforehand with a 20 mM potassium phosphate buffer (pH 6.0) containing 1.2 M ammonium sulfate, and the enzyme was eluted with a linear concentration gradient of 1 to 0 M ammonium sulfate. Among the eluted fractions, fractions that showed the γ-Glu-Val synthesis activity were collected as an active fraction (total protein amount 2.7 mg, total activity 1.7 U).

(4) Gel Filtration Chromatography

The active fraction obtained in (3) mentioned above was concentrated with Amicon Ultra Filter Unit 10,000 NMWL (Merck Millipore), and applied to a HiLoad 16/600 Superdex 200 pg column (GE Healthcare) equilibrated beforehand with a 20 mM potassium phosphate buffer (pH 6.0), and the enzyme was eluted. Among the eluted fractions, fractions that showed the γ-Glu-Val synthesis activity were collected as an active fraction (total protein amount 0.3 mg, total activity 0.8 U).

(5) Hydrophobic Interaction Chromatography

The active fraction obtained in (4) mentioned above was mixed with the same volume of a 20 mM potassium phosphate buffer (pH 6.0) containing 2.4 M ammonium sulfate, the mixture was applied to a RESOURCE PHE 1 ml column (GE Healthcare) equilibrated beforehand with a 20 mM potassium phosphate buffer (pH 6.0) containing 1.2 M ammonium sulfate, and the enzyme was eluted with a linear concentration gradient of 1 to 0 M ammonium sulfate. Among the eluted fractions, fractions that showed the γ-Glu-Val synthesis activity were collected as a purified enzyme. The purified enzyme was subjected to polyacrylamide gel electrophoresis, and the gel was stained with Coomassie Brilliant Blue (CBB). On the basis of the fractions that showed the activity, and the electrophoresis pattern, a band of a molecular weight of about 40,000 corresponding to γ-Glu-Val synthetase was identified.

Example 3 Determination of Partial Amino Acid Sequence of γ-Glu-Val Synthetase Derived from *Kocuria Rosea* (AJ3132) and Nucleotide Sequence of Gene Encoding this Enzyme The purified enzyme obtained in Example 2 was subjected to SDS-polyacrylamide gel electrophoresis, and transferred to a PVDF membrane, and the N-terminus amino acid sequence of ten residues (SEQ ID NO: 1) was determined on a protein sequencer. Further, the purified enzyme obtained in Example 2 was subjected to SDS-polyacrylamide gel electrophoresis, and then digested with trypsin, a fragment was isolated by reverse phase HPLC, and an internal amino acid sequence of 14 residues thereof (SEQ ID NO: 2) was determined on a protein sequencer.

Then, the genomic DNA of *Kocuria rosea* (AJ3132) was prepared by using Nextera XT (Illumina), and the sequence thereof was analyzed with Miseq (Illumina) according to the attached protocol. As a result, an ORF region (SEQ ID NO: 3) containing nucleotide sequences encoding the N-terminus amino acid sequence and internal amino acid sequence was found.

Example 4 Expression of γ-Glu-Val Synthetase Derived from *Kocuria Rosea* (AJ3132) in *Escherichia Coli*

(1) Construction of Expression Strain for γ-Glu-Val Synthetase Derived from *Kocuria Rosea* (AJ3132)

An expression plasmid pET-KrogshA for the gene encoding the γ-Glu-Val synthetase derived from *Kocuria rosea* (AJ3132) found in Example 3 (ORF region of SEQ ID NO: 3) was constructed according to the following procedures. Since the start codon of this gene was GTG, the start codon was replaced with ATG, when pET-KrogshA was constructed.

First, PCR was performed by using the genomic DNA of *Kocuria rosea* (AJ3132) as the template, and KOD-plus- (Toyobo) as the polymerase for 30 cycles under the conditions of 98° C. for 30 seconds, and 67° C. for 1 minute according to the protocol of the manufacturer to amplify the ORF region of SEQ ID NO: 3 of about 1.1 kb. As the primers, the combination of the primers of SEQ ID NOS: 4 and 5 was used. Then, the obtained PCR product was digested with NdeI/HindIII, and the objective DNA of about 1.1 kb was separated by agarose gel electrophoresis, and ligated with pET21a(+) digested beforehand with NdeI/HindIII by using Ligation-Convenience Kit (NIPPON GENE). The *Escherichia coli* JM109 strain was transformed with the ligation reaction mixture, applied to the LB agar medium (1.0% (w/v) peptone, 0.5% (w/v) yeast extract, 1.0% (w/v) NaCl, 1.5% (w/v) agar) containing 100 mg/L of Amp, and cultured overnight at 30° C. Plasmids were extracted from the colonies of the grown transformants by a known method, the nucleotide sequences thereof were confirmed by using 3100 Genetic Analyzer (Applied-Biosystems), and a plasmid having the objective structure was named pET-KrogshA. *Escherichia coli* BL21(DE3) was transformed with the obtained pET-KrogshA to obtain a transformant having pET-KrogshA. This transformant was designated as *Escherichia coli* BL21(DE3)/pET-KrogshA.

(2) Purification of γ-Glu-Val Synthetase Derived from *Kocuria rosea* (AJ3132) and Expressed in *Escherichia coli*

*Escherichia coli* BL21(DE3)/pET-KrogshA was cultured overnight at 30° C. on the LB agar medium containing 100 mg/L of Amp. The obtained cells were inoculated into 200 ml of OVERNIGHT EXPRESS™ Instant TB medium (Novagen), the medium was put into 500 ml-volume Sakaguchi flasks in a volume of 100 ml each, and culture was performed at 37° C. for 16 hours with shaking by reciprocal movement of 110 times/minute. The cells were collected by centrifugation (12,000 g, 5 minutes), washed with a 20 mM potassium phosphate buffer (pH 6.0), and made into a cell suspension by using the same buffer. The cell suspension was subjected to ultrasonication to disrupt the cells, and centrifuged (29,100 g, 20 minutes) to obtain a supernatant as a cell-free extract.

The obtained cell-free extract was applied to a HiLoad 16/10 Q Sepharose High Performance column (GE Healthcare) equilibrated beforehand with a 20 mM potassium phosphate buffer (pH 6.0), and the enzyme was eluted with a linear concentration gradient of 0 to 1 M sodium chloride to obtain an active fraction.

The obtained active fraction was mixed with the same volume of a 20 mM potassium phosphate buffer (pH 6.0) containing 2.4 M ammonium sulfate, and the mixture was gently stirred at 4° C. for 3 hours, and then centrifuged (12,000 g, 5 minutes) to obtain a supernatant. The obtained supernatant was applied to connected two HiTrap Phenyl High Performance 5 ml columns (GE Healthcare) equilibrated beforehand with a 20 mM potassium phosphate buffer (pH 6.0) containing 1.2 M ammonium sulfate, and the enzyme was eluted with a linear concentration gradient of 1 to 0 M ammonium sulfate to obtain an active fraction.

The obtained active fraction was dialyzed against a 20 mM potassium phosphate buffer (pH 6.0) containing 15% (w/v) glycerol. The dialyzed enzyme solution was subjected to polyacrylamide gel electrophoresis, and the gel was stained with a CBB staining solution. As a result, a uniform band was detected at a position of a molecular weight of about 40,000.

An appropriate volume of the dialyzed enzyme solution was added to a reaction mixture 2 (100 mmol/L Tris-HCl buffer, 10 mmol/L Glu, 10 mmol/L Val, 10 mmol/L ATP, 10 mmol/L magnesium sulfate, pH 9.0), and the reaction was performed at 30° C. for 30 minutes. After completion of the reaction, γ-Glu-Val was quantified in the same manner as that of Example 1. In Example 4, the enzymatic activity for generating 1 μmol of γ-Glu-Val in 1 minute under these conditions was defined as 1 U of the γ-Glu-Val synthesis activity. The dialyzed enzyme solution had the γ-Glu-Val synthesis activity, and the specific activity thereof was 0.883 U/mg. On the basis of these results, the ORF region of SEQ ID NO: 3 was designated as KrogshA, and the protein encoded by KrogshA was designated as KroGSHA (SEQ ID NO: 6). The dialyzed enzyme solution was used for the following experiments as purified KroGSHA.

Example 5 Expression of γ-Glu-Val Synthetase Derived from *Kocuria Rhizophila* DC2201 Strain (KrhgshA) in *Escherichia Coli*

(1) Construction of Expression Strain for γ-Glu-Val Synthetase Derived from *Kocuria Rhizophila* DC2201 Strain An expression plasmid pQE-KrhgshA for the KrhgshA gene (SEQ ID NO: 7) encoding the γ-Glu-Val synthetase of the *Kocuria rhizophila* DC2201 strain (ATCC 9341) was constructed according to the following procedures.

PCR was performed by using the genomic DNA of the *Kocuria rhizophila* DC2201 strain as the template, and KOD-plus-(Toyobo) as the polymerase for 30 cycles under the conditions of 98° C. for 30 seconds, and 67° C. for 1 minute according to the protocol of the manufacturer to amplify the ORF region of SEQ ID NO: 7 of about 1.2 kb. As the primers, the combination of the primers of SEQ ID NOS: 8 and 9 was used. The obtained PCR product was digested with KpnI/HindIII, and the objective DNA of about 1.2 kb was separated by agarose gel electrophoresis, and ligated with pQE30 digested beforehand with KpnI/HindIII by using Ligation-Convenience Kit (NIPPON GENE). The *Escherichia coli* JM109 strain was transformed with the ligation reaction mixture, applied to the LB agar medium containing 100 mg/L of Amp, and cultured overnight at 30° C. Plasmids were extracted from the colonies of the grown transformants by a known method, the nucleotide sequences thereof were confirmed by using 3100 Genetic Analyzer (Applied-Biosystems), and a plasmid having the objective structure was named pQE-KrhgshA. Further, the transformant having this plasmid was named *Escherichia coli* JM109/pQE-KrhgshA. The nucleotide sequence of the KrhgshA gene and the amino acid sequence of KrhGSHA encoded thereby are shown as SEQ ID NOS: 7 and 10, respectively. With pQE-KrhgshA, KrhGSHA is expressed with a His tag added to the N-terminus.

(2) Purification of Recombinant KrhGSHA with His Tag Added to N-Terminus

*Escherichia coli* JM109/pQE-KrhgshA was cultured overnight at 30° C. on the LB agar medium containing 100 mg/L of Amp. The obtained cells were inoculated into 500 ml of the TB medium (Terrific Broth (Sambrook, J. et al., Molecular Cloning: A Laboratory Manual, 3rd Edition, Cold Spring Harbor Laboratory Press (2001)), the medium was put into 500 ml-volume Sakaguchi flasks in a volume of 100 ml each, and culture was performed at 30° C. for 16 hours with shaking by reciprocal movement of 110 times/minute. The cells were collected by centrifugation (12,000 g, 5 minutes), washed with a 20 mM potassium phosphate buffer (pH 6.0), and made into a cell suspension by using an eluent A (20 mM potassium phosphate buffer (pH 6.0) containing 300 mM NaCl and 10 mM imidazole). The cell suspension was subjected to ultrasonication to disrupt the cells, and centrifuged (29,100 g, 20 minutes) to obtain a supernatant as a cell-free extract.

The obtained cell-free extract was applied to a HisTALON 5 ml column (Clontech) equilibrated beforehand with the eluent A, and the enzyme was eluted with a linear concentration gradient of 10 to 150 mM imidazole to obtain an active fraction.

The obtained active fraction was mixed with the same volume of a 20 mM potassium phosphate buffer (pH 6.0) containing 2.4 M ammonium sulfate, and the mixture was gently stirred at 4° C. for 3 hours, and then centrifuged (12,000 g, 5 minutes) to obtain a supernatant. The obtained supernatant was applied to a HiTrap Phenyl High Performance 1 ml column (GE Healthcare) equilibrated beforehand with a 20 mM potassium phosphate buffer (pH 6.0) containing 1.2 M ammonium sulfate, and the enzyme was eluted with a linear concentration gradient of 1 to 0 M ammonium sulfate to obtain an active fraction.

The obtained active fraction was dialyzed against a 20 mM potassium phosphate buffer (pH 6.0) containing 15% (w/v) glycerol. The dialyzed enzyme solution was used for the following experiments as purified KrhGSHA.

Example 6 Expression of γ-Glu-Val Synthetase Derived from *Micrococcus Luteus* NCTC2665 Strain (MluGSHA) in *Escherichia Coli*

(1) Construction of Expression Strain for γ-Glu-Val Synthetase Derived from *Micrococcus Luteus* NCTC2665 Strain An expression plasmid pQE-MlugshA for the MlugshA gene (SEQ ID NO: 11) encoding the γ-Glu-Val synthetase of the *Micrococcus luteus* NCTC2665 strain (ATCC 15307) was constructed according to the following procedures.

PCR was performed by using the genomic DNA of the *Micrococcus luteus* NCTC2665 strain as the template, and KOD-plus-(Toyobo) as the polymerase for 30 cycles under the conditions of 98° C. for 30 seconds, and 67° C. for 1 minute according to the protocol of the manufacturer to amplify the ORF region of SEQ ID NO: 11 of about 1.2 kb. As the primers, the combination of the primers of SEQ ID NOS: 12 and 13 was used. The obtained PCR product was digested with BamHI/HindIII, and the objective DNA of about 1.2 kb was separated by agarose gel electrophoresis, and ligated with pQE30 digested beforehand with BamHI/HindIII by using Ligation-Convenience Kit (NIPPON GENE). The *Escherichia coli* JM109 strain was transformed with the ligation reaction mixture, applied to the LB agar medium containing 100 mg/L of Amp, and cultured overnight at 30° C. Plasmids were extracted from the colonies of the grown transformants by a known method, and the nucleotide sequences thereof were confirmed by using 3100 Genetic Analyzer (Applied-Biosystems). As a result, it was found that the nucleotide sequence CAG encoding glutamine of the position 263 in the amino acid sequence of MluGSHA was replaced with TAG, which is a stop codon. Therefore, a mutation for replacing TAG with CAG was introduced into an obtained plasmid by the following procedures. PCR was performed by using the obtained plasmid as the template, and the primers of the sequences of SEQ ID NOS: 14 and 15 with "Quik Change Site-Directed Mutagenesis Kit" of Stratagene according to the protocol of the manufacturer. The obtained PCR product was digested with DpnI. The *Escherichia coli* JM109 strain was transformed with the digestion reaction mixture, applied to the LB agar medium containing 100 mg/L of Amp, and cultured overnight at 30° C. Plasmids were extracted from the colonies of the grown transformants by a known method, the nucleotide sequences thereof were confirmed by using 3100 Genetic Analyzer (Applied-Biosystems), and a plasmid having the objective structure was named pQE-MlugshA. The transformant having this plasmid was named *Escherichia coli* JM109/pQE-MlugshA. The nucleotide sequence of the MlugshA gene and the amino acid sequence of MluGSHA encoded by that gene are shown as SEQ ID NOS: 11 and 16, respectively. With pQE-MlugshA, MluGSHA is expressed with a His tag added to the N-terminus.

(2) Purification of Recombinant MluGSHA with His Tag Added to N-Terminus

*Escherichia coli* JM109/pQE-MlugshA was cultured overnight at 30° C. on the LB agar medium containing 100 mg/L of Amp. The obtained cells were inoculated into 500 ml of the TB medium, the medium was put into 500 ml-volume Sakaguchi flasks in a volume of 100 ml each, and culture was performed at 30° C. for 16 hours with shaking by reciprocal movement of 110 times/minute. The cells were collected by centrifugation (12,000 g, 5 minutes), washed with a 20 mM potassium phosphate buffer (pH 6.0), and made into a cell suspension by using the eluent A. The cell suspension was subjected to ultrasonication to disrupt the cells, and centrifuged (29,100 g, 20 minutes) to obtain a supernatant as a cell-free extract.

The obtained cell-free extract was applied to a HisTALON 5 ml column (Clontech) equilibrated beforehand with the eluent A, and the enzyme was eluted with a linear concentration gradient of 10 to 150 mM imidazole to obtain an active fraction.

The obtained active fraction was mixed with the same volume of a 20 mM potassium phosphate buffer (pH 6.0) containing 2.4 M ammonium sulfate, and the mixture was gently stirred at 4° C. for 3 hours, and then centrifuged (12,000 g, 5 minutes) to obtain a supernatant. The obtained supernatant was applied to a HiTrap Phenyl High Performance 1 ml column (GE Healthcare) equilibrated beforehand with a 20 mM potassium phosphate buffer (pH 6.0) containing 1.2 M ammonium sulfate, and the enzyme was eluted with a linear concentration gradient of 1 to 0 M ammonium sulfate to obtain an active fraction.

The obtained active fraction was dialyzed against a 20 mM potassium phosphate buffer (pH 6.0) containing 15% (w/v) glycerol. The dialyzed enzyme solution was used for the following experiments as purified MluGSHA.

Example 7 Expression of γ-Glu-Val Synthetase Derived from *Corynebacterium Glutamicum* K051 Strain (CglGSHA) in *Escherichia Coli*

(1) Construction of Expression Strain for γ-Glu-Val Synthetase Derived from *Corynebacterium Glutamicum* K051 Strain An expression plasmid pET-CglgshA for the CglgshA gene (SEQ ID NO: 17) encoding the γ-Glu-Val synthetase of the *Corynebacterium glutamicum* K051 strain (ATCC 13032) was constructed according to the following procedures.

The ORF region of SEQ ID NO: 17 contained a XhoI recognition site. Therefore, the full length of the ORF region in which the XhoI recognition site was deleted (CTCGAG at the positions 145 to 150 in SEQ ID NO: 17 was replaced with CTGGAG) was obtained by two-step PCR.

PCR at the first step was performed by using the genomic DNA of the *Corynebacterium glutamicum* K051 strain as the template, and KOD-plus-(Toyobo) as the polymerase for 30 cycles under the conditions of 98° C. for 30 seconds, and 67° C. for 1 minute according to the protocol of the manufacturer to separately amplify an upstream part and downstream part of the ORF region of about 1.2 kb. As the primers, the combination of the primers of SEQ ID NOS: 18 and 19 was used for the amplification of the upstream part, and the combination of the primers of SEQ ID NOS: 20 and 21 was used for the amplification of the downstream part. Then, the obtained PCR products were subjected to agarose gel electrophoresis to separate the objective DNA fragments of about 160 b and about 1.0 kb.

PCR at the second step was performed by using the two kinds of fragments obtained by PCR at the first step as the template under the same PCR conditions as those of PCR at the first step to amplify the full length of the ORF region of about 1.2 kb deficient in the XhoI recognition site. As the primers, the combination of the primers of SEQ ID NOS: 18 and 21 was used. The obtained PCR product was digested with NdeI/XhoI, and the objective DNA of about 1.2 kb was separated by agarose gel electrophoresis, and ligated with pET21a(+) digested beforehand with NdeI/XhoI by using Ligation-Convenience Kit (NIPPON GENE). The *Escherichia coli* JM109 strain was transformed with the ligation reaction mixture, applied to the LB agar medium containing 100 mg/L of Amp, and cultured overnight at 30° C. Plasmids were extracted from the colonies of the grown transformants by a known method, and the nucleotide sequences thereof were confirmed by using 3100 Genetic Analyzer (Applied-Biosystems), and a plasmid having the objective structure was named pET-CglgshA. *Escherichia coli* BL21(DE3) was transformed with the obtained pET-CglgshA to obtain a transformant having pET-CglgshA. This transformant was designated as *Escherichia coli* BL21(DE3)/pET-CglgshA. The nucleotide sequence of the CglgshA gene and the amino acid sequence encoded thereby are shown as SEQ ID NOS: 17 and 22, respectively. With pET-CglgshA, CglGSHA is expressed with a His tag added to the C-terminus.

(2) Purification of Recombinant CglGSHA with His Tag Added to C-Terminus

*Escherichia coli* BL21(DE3)/pET-CglgshA was cultured overnight at 30° C. on the LB agar medium containing 100 mg/L of Amp. The obtained cells were inoculated into 100 ml of OVERNIGHT EXPRESS™ Instant TB medium (Novagen), and cultured at 30° C. for 16 hours in a 500 ml-volume Sakaguchi flask with shaking by reciprocal movement of 110 times/minute. The cells were collected by centrifugation (12,000 g, 5 minutes), washed with a 20 mM potassium phosphate buffer (pH 6.0), and made into a cell suspension by using the eluent A containing 300 mM NaCl. The cell suspension was subjected to ultrasonication to disrupt the cells, and centrifuged (29,100 g, 20 minutes) to obtain a supernatant as a cell-free extract.

The obtained cell-free extract was applied to a HisTALON 5 ml column (Clontech) equilibrated beforehand with the eluent A, and the enzyme was eluted with a linear concentration gradient of 10 to 150 mM imidazole to obtain an active fraction.

The obtained active fraction was dialyzed against a 20 mM potassium phosphate buffer (pH 6.0) containing 15% (w/v) glycerol. The dialyzed enzyme solution was used for the following experiments as purified CglGSHA.

Example 8 Purification of Recombinant GSH1 Derived from *Saccharomyces Cerevisiae* S288C Strain (ScGSH1) with His Tag Added to C-Terminus An expression plasmid pET-ScGSH1 for the GSH1 gene (ScGSH1 gene, SEQ ID NO: 23) encoding glutamate-cysteine ligase of the *Saccharomyces cerevisiae* S288C strain (ATCC 26108) was constructed by the method described in Japanese Patent Laid-open (Kokai) No. 2012-85637. Then, *Escherichia coli* BL21(DE3) was transformed with pET-ScGSH1 to obtain *Escherichia coli* BL21(DE3)/pET-ScGSH1. The nucleotide sequence of the ScGSH1 gene and the amino acid sequence of ScGSH1 encoded by that gene are shown as SEQ ID NOS: 23 and 24, respectively. With pET-ScGSH1, ScGSH1 is expressed with a His tag added to the C-terminus.

*Escherichia coli* BL21(DE3)/pET-ScGSH1 was cultured overnight at 30° C. on the LB agar medium containing 100 mg/L of Amp. The obtained cells were inoculated into 50 ml of the LB medium, and cultured at 37° C. for 16 hours in a 500 ml-volume Sakaguchi flask with shaking by reciprocal movement of 110 times/minute. A 2 ml aliquot of the obtained culture broth was inoculated into 100 ml of the LB medium contained in a Sakaguchi flask. Culture was performed at 37° C. for 2 hours with shaking by reciprocal movement of 110 times/minute, then isopropyl-β-D-thiogalactopyranoside (IPTG) was added at a final concentration of 0.5 mmol/L, and culture was further performed at 30° C. for 4 hours. The cells were collected by centrifugation (12,000 g, 5 minutes), washed with an eluent B (20 mM Tris-HCl buffer (pH 8.0) containing 300 mM NaCl, 10 mM imidazole, and 15% (w/v) glycerol), and made into a cell suspension by using the eluent B. The cell suspension was subjected to ultrasonication to disrupt the cells, and centrifuged (29,100 g, 20 minutes) to obtain a supernatant as a cell-free extract.

The obtained cell-free extract was applied to a HisTALON 5 ml column (Clontech) equilibrated beforehand with the eluent C, and the enzyme was eluted with a linear concentration gradient of 10 to 150 mM imidazole to obtain an active fraction.

The obtained active fraction was dialyzed against a Tris-HCl buffer (pH 8.0) containing 300 mM NaCl and 15% (w/v) glycerol. The dialyzed enzyme solution was used for the following experiments as purified ScGSH1.

Example 9 Purification of Recombinant GSHA Derived from *Escherichia coli* K-12 W3110 Strain (EcGSHA) with His Tag Added to N-Terminus An expression plasmid pQE-EcgshA for the gshA gene (EcgshA gene, SEQ ID NO: 25) encoding glutamate-cysteine ligase of the *Escherichia coli* K-12 W3110 strain (ATCC 27325) was constructed by the method described in Japanese Patent Laid-open (Kokai) No. 2012-85637. Then, *Escherichia coli* BL21(DE3) was transformed with pQE-EcgshA to obtain *Escherichia coli* BL21(DE3)/pQE-EcgshA. The nucleotide sequence of the EcgshA gene and the amino acid sequence of EcGSHA encoded by that gene are shown as SEQ ID NOS: 25 and 26, respectively. With pQE-EcgshA, EcGSHA is expressed with a His tag added to the N-terminus.

*Escherichia coli* BL21(DE3)/pQE-EcgshA was cultured by the same method as that used in Japanese Patent Laid-open (Kokai) No. 2012-85637. The cells were collected by centrifugation (12,000 g, 5 minutes), washed with the eluent C (20 mM Tris-HCl buffer (pH 7.6) containing 300 mM NaCl and 10 mM imidazole), and made into a cell suspension by using the eluent C. The cell suspension was subjected to ultrasonication to disrupt the cells, and centrifuged (29,100 g, 20 minutes) to obtain a supernatant as a cell-free extract.

The obtained cell-free extract was applied to a HisTALON 5 ml column (Clontech) equilibrated beforehand with the eluent C, and the enzyme was eluted with a linear concentration gradient of 10 to 150 mM imidazole to obtain an active fraction.

The obtained active fraction was dialyzed against 20 mM Tris-HCl (pH 7.6). The dialyzed enzyme solution was used for the following experiments as purified EcGSHA.

Example 10 Purification of Recombinant GSHB Derived from *Escherichia Coli* K-12 W3110 Strain (EcGSHB) with His Tag Added to C-Terminus An expression plasmid pQE-EcgshB for the gshB gene (EcgshB gene, SEQ ID NO: 27) encoding glutathione synthetase of the *Escherichia coli* K-12 W3110 strain (ATCC 27325) was constructed by the method described in Japanese Patent Laid-open (Kokai) No. 2012-85637. Then, *Escherichia coli* BL21(DE3) was transformed with pQE-EcgshB to obtain *Escherichia coli* BL21(DE3)/pQE-EcgshB. The nucleotide sequence of the EcgshB gene and the amino acid sequence of EcGSHB encoded by that gene are shown as SEQ ID NOS: 27 and 28, respectively. With pQE-EcgshB, EcGSHB is expressed with a His tag added to the C-terminus.

This strain was cultured by the same method as that used in Japanese Patent Laid-open (Kokai) No. 2012-85637. The cells were collected by centrifugation (12,000 g, 5 minutes), washed with the eluent C, and made into a cell suspension by using the eluent C. The cell suspension was subjected to ultrasonication to disrupt the cells, and centrifuged (29,100 g, 20 minutes) to obtain a supernatant as a cell-free extract.

The obtained cell-free extract was applied to a HisTALON 5 ml column (Clontech) equilibrated beforehand with the eluent C, and the enzyme was eluted with a linear concentration gradient of 10 to 150 mM imidazole to obtain an active fraction.

The obtained active fraction was dialyzed against 20 mM Tris-HCl (pH 7.6). The dialyzed enzyme solution was used for the following experiments as purified EcGSHB.

Example 11 Generation of γ-Glutamyl Dipeptides with Purified GSHAs

The γ-Glu-Val synthesis activity and γ-Glu-Gly synthesis activity of the purified GSHAs obtained in Examples 4 to 9

(ScGSH1, EcGSHA, KroGSHA, KrhGSHA, MluGSHA, and CglGSHA) were measured.

<Measurement of γ-Glu-Val Synthesis Activity>

An appropriate amount of each of the purified GSHAs was added to the reaction mixture 2 mentioned in Example 4 (100 mmol/L Tris-HCl buffer, 10 mmol/L Glu, 10 mmol/L Val, 10 mmol/L ATP, 10 mmol/L magnesium sulfate, pH 9.0), and the reaction was performed at 30° C. for 30 minutes. After completion of the reaction, γ-Glu-Val was quantified in the same manner as that of Example 1. In Example 11, the enzymatic activity for generating 1 μmol of γ-Glu-Val in 1 minute under these conditions was defined as 1 U of the γ-Glu-Val synthesis activity.

<Measurement of γ-Glu-Gly Synthesis Activity>

An appropriate amount of each of the purified GSHAs was added to a reaction mixture 3 (100 mmol/L Tris-HCl buffer, 10 mmol/L Glu, 10 mmol/L Gly, 10 mmol/L ATP, 10 mmol/L magnesium sulfate, pH 9.0), and the reaction was performed at 30° C. for 30 minutes. After completion of the reaction, γ-Glu-Gly was quantified by HPLC. In Example 11, the enzymatic activity for generating 1 μmol of γ-Glu-Gly in 1 minute under these conditions was defined as 1 U of the γ-Glu-Gly synthesis activity.

The quantification conditions for γ-Glu-Gly were as follows. Inertsil ODS-3 produced by GL Science (particle size 5 microns, inner diameter 4.6 mm, length 250 mm) was used as the column. As the eluent, a mixture of a solution A (30 mM potassium dihydrogenphosphate, 10 mM sodium octanesulfonate (pH 2.0, adjusted with phosphoric acid)), and a solution B (acetonitrile) mixed at a ratio of 85:15 (v/v) was used. The column temperature was 40° C., and UV detection wavelength was 210 nm.

The γ-Glu-Val synthesis activity and γ-Glu-Gly synthesis activity were measured as specific activities by the methods described above, and a ratio (B)/(A), which is a ratio of (B) γ-Glu-Val synthesis activity (specific activity) to (A) γ-Glu-Gly synthesis activity (specific activity), was calculated. The results are shown in Table 2.

TABLE 2

| Enzyme | Reaction (A) Glu + Gly + ATP (U/mg) | Reaction (B) Glu + Val + ATP (U/mg) | (B)/(A) |
|---|---|---|---|
| ScGSH1 | 0.195 | 0.014 | 0.1 |
| EcGSHA | 0.772 | 0.153 | 0.2 |
| KroGSHA | 0.038 | 0.883 | 23.4 |
| KrhGSHA | 0.001 | 0.020 | 30.6 |
| MluGSHA | 0.038 | 0.620 | 16.5 |
| CglGSHA | 0.001 | 0.003 | 2.6 |

Example 12 Generation of γ-Glutamyl Tripeptides from Amino Acids Using Purified GSHAs and Purified EcGSHB By using each of the purified GSHAs obtained in Examples 4 to 9 (ScGSH1, EcGSHA, KroGSHA, KrhGSHA, MluGSHA, and CglGSHA), and the purified EcGSHB obtained in Example 10, generation of γ-glutamyl tripeptide such as γ-Glu-Val-Gly (CAS 38837-70-6, also referred to as "gluvalicine") from amino acids was examined. The structural formula of γ-Glu-Val-Gly is shown below as the formula (I).

[Formula 1]

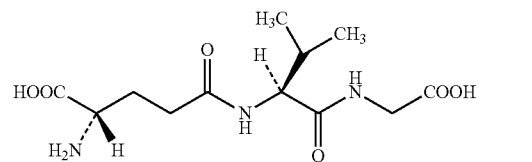

Formula (I)

Each of the purified GSHAs and the purified EcGSHB were added to a reaction mixture 4 (50 mmol/L Tris-HCl buffer, 100 mmol/L Glu, 100 mmol/L Val, 100 mmol/L Gly, 10 mmol/L ATP, 10 mmol/L magnesium sulfate, 240 mmol/L phosphoenolpyruvic acid, 20000 U/L pyruvate kinase, pH 8.5), and the reaction was performed at 30° C. For this reaction, the enzymes were added to the reaction mixture 4 at concentrations of 0.2 g/l for the purified EcGSHA, 0.1 g/l for the purified KroGSHA and the purified MluGSHA, 1 g/l for the purified KrhGSHA and the purified CglGSHA, and 0.4 g/l for the purified GSHB.

One hour after the start of the reaction, γ-Glu-Val and γ-Glu-Val-Gly were analyzed by the same method as that for the quantification of γ-Glu-Val used in Example 1, and γ-Glu-Gly and γ-Glu-Gly-Gly were analyzed by the same method as that for the quantification of γ-Glu-Gly used in Example 11, to thereby calculate the generation amounts of these ingredients. The results are shown in Table 3. From these results, (C) the total amount of γ-Glu-Gly and γ-Glu-Gly-Gly, and (D) the total amount of γ-Glu-Val and γ-Glu-Val-Gly were calculated, and a ratio (D)/(C), which is a ratio of (D) the total amount of γ-Glu-Val and γ-Glu-Val-Gly to (C) the total amount of γ-Glu-Gly and γ-Glu-Gly-Gly, was calculated. The results are shown in Table 4. A correlation diagram for the ratio (B)/(A), which is a ratio of the γ-Glu-Val synthesis activity to the γ-Glu-Gly synthesis activity, shown in Example 11, Table 2, and the ratio (D)/(C), which is a ratio of the total amount of γ-Glu-Val and γ-Glu-Val-Gly to the total amount of γ-Glu-Gly and γ-Glu-Gly-Gly, is shown in the FIGURE. The Pearson's product-moment correlation coefficient between (B)/(A) and (D)/(C) was calculated to be 0.991, and therefore a positive correlation was observed between (B)/(A) and (D)/(C).

TABLE 3

| Enzyme | | γ-Glu-Gly (mmol/L) | γ-Glu-Gly-Gly (mmol/L) | γ-Glu-Val (mmol/L) | γ-Glu-Val-Gly (mmol/L) |
|---|---|---|---|---|---|
| ScGSH1 | EcGSHB | 50.2 | 21.3 | 9.8 | 0.2 |
| EcGSHA | EcGSHB | 32.3 | 30.3 | 3.7 | 0.1 |
| KroGSHA | EcGSHB | 0.2 | 0.6 | 19.0 | 19.8 |
| KrhGSHA | EcGSHB | 0.1 | 0.4 | 12.3 | 15.1 |
| MluGSHA | EcGSHB | 0.1 | 0.4 | 3.9 | 10.4 |
| CglGSHA | EcGSHB | 0.5 | 2.9 | 0.5 | 2.5 |

TABLE 4

| Enzyme | | (C) γ-Glu-Gly + γ-Glu-Gly-Gly (mmol/L) | (D) γ-Glu-Val + γ-Glu-Val-Gly (mmol/L) | (D)/(C) |
|---|---|---|---|---|
| ScGSH1 | EcGSHB | 71.5 | 10.0 | 0.1 |
| EcGSHA | EcGSHB | 62.6 | 3.8 | 0.1 |
| KroGSHA | EcGSHB | 0.9 | 38.9 | 44.9 |
| KrhGSHA | EcGSHB | 0.5 | 27.4 | 53.0 |

TABLE 4-continued

| Enzyme | | (C)<br>γ-Glu-Gly +<br>γ-Glu-Gly-<br>Gly<br>(mmol/L) | (D)<br>γ-Glu-Val +<br>γ-Glu-Val-<br>Gly<br>(mmol/L) | (D)/(C) |
|---|---|---|---|---|
| MluGSHA | EcGSHB | 0.5 | 14.4 | 31.3 |
| CglGSHA | EcGSHB | 3.4 | 3.0 | 0.9 |

Twenty-four hours after the start of the reaction, the amount of the generated γ-Glu-Val-Gly was calculated in the same manner as described above. The results are shown in Table 5.

TABLE 5

| Enzyme | | γ-Glu-Val-Gly<br>(mmol/L) |
|---|---|---|
| ScGSH1 | EcGSHB | 0.3 |
| EcGSHA | EcGSHB | 0.2 |
| KroGSHA | EcGSHB | 85.6 |
| KrhGSHA | EcGSHB | 86.9 |
| MluGSHA | EcGSHB | 45.0 |
| CglGSHA | EcGSHB | 33.5 |

INDUSTRIAL APPLICABILITY

γ-Glu-Val synthetase of the present invention catalyzes the γ-Glu-Val generation reaction with selectively using Val as a substrate. Therefore, according to the present invention, γ-Glu-Val can be efficiently produced by using γ-Glu-Val synthetase of the present invention with Glu and Val as raw materials, and γ-Glu-Val-Gly can further be produced by using γ-Glu-Val and Gly as raw materials. Also, according to the present invention, γ-Glu-Val-Gly can be efficiently produced by using γ-Glu-Val synthetase of the present invention with Glu, Val, and Gly as raw materials.

<Explanation of Sequence Listing>
SEQ ID NO: 1, N-terminus amino acid sequence of KroGSHA protein of *Kocuria rosea* (AJ3132)
SEQ ID NO: 2, Internal amino acid sequence of KroGSHA protein of *Kocuria rosea* (AJ3132)
SEQ ID NO: 3, Nucleotide sequence of KrogshA gene of *Kocuria rosea* (AJ3132)
SEQ ID NOS: 4 and 5, Primers
SEQ ID NO: 6, Amino acid sequence of KroGSHA protein of *Kocuria rosea* (AJ3132)
SEQ ID NO: 7, Nucleotide sequence of KrhgshA gene of *Kocuria rhizophila* DC2201 strain
SEQ ID NOS: 8 and 9, Primers
SEQ ID NO: 10, Amino acid sequence of KrhGSHA protein of *Kocuria rhizophila* DC2201 strain
SEQ ID NO: 11, Nucleotide sequence of MlugshA gene of *Micrococcus luteus* NCTC2665 strain
SEQ ID NOS: 12 to 15, Primers
SEQ ID NO: 16, Amino acid sequence of MluGSHA protein of *Micrococcus luteus* NCTC2665 strain
SEQ ID NO: 17, Nucleotide sequence of CglgshA gene of *Corynebacterium glutamicum* K051 strain
SEQ ID NOS: 18 to 21, Primers
SEQ ID NO: 22, Amino acid sequence of CglGSHA protein of *Corynebacterium glutamicum* K051 strain
SEQ ID NO: 23, Nucleotide sequence of ScGSH1 gene of *Saccharomyces cerevisiae* S288C strain
SEQ ID NO: 24, Amino acid sequence of ScGSH1 protein of *Saccharomyces cerevisiae* S288C strain
SEQ ID NO: 25, Nucleotide sequence of EcgshA gene of *Escherichia coli* K-12 W3110 strain
SEQ ID NO: 26, Amino acid sequence of EcGSHA protein of *Escherichia coli* K-12 W3110 strain
SEQ ID NO: 27, Nucleotide sequence of EcgshB gene of *Escherichia coli* K-12 W3110 strain
SEQ ID NO: 28, Amino acid sequence of EcGSHB protein of *Escherichia coli* K-12 W3110 strain
SEQ ID NO: 29, Nucleotide sequence of ggt gene of *Escherichia coli* K-12 MG1655 strain
SEQ ID NO: 30, Amino acid sequence of GGT of *Escherichia coli* K-12 MG1655 strain

The invention claimed is:

1. A method for producing γ-Glu-Val-Gly and/or a salt thereof, the method comprising:
contacting a protein and glutathione synthetase with Glu, Val, and Gly to produce γ-Glu-Val-Gly; and
collecting the produced γ-Glu-Val-Gly,
wherein the protein comprises an amino acid sequence having at least 97% sequence identity to the amino acid sequence of SEQ ID NO: 6, 10, or 16, and has γ-glutamylvaline synthetase activity, and
a ratio of γ-glutamylvaline synthetase activity of the protein to γ-glutamylglycine synthetase activity of the protein is 15 or higher.

2. The method according to claim 1, wherein the protein is purified.

3. The method according to claim 1, wherein the protein is immobilized.

4. The method according to claim 1, wherein the contacting of the protein and glutathione synthetase is carried out in the presence of ATP.

5. The method according to claim 1, wherein the ratio of γ-glutamylvaline synthetase activity of the protein to γ-glutamylglycine synthetase activity of the protein is 20 or higher.

6. The method according to claim 1, wherein the protein is contained in a culture broth of a microorganism having the protein, cultured cells of the microorganism, or a processed product of the cultured cells.

7. The method according to claim 1, wherein the protein and the glutathione synthetase are contained in a culture broth of a microorganism having the protein and the glutathione synthetase, cultured cells of the microorganism, or a processed product of the cultured cells.

8. The method according to claim 6, wherein the microorganism has been modified so that γ-glutamyltransferase activity is reduced as compared to γ-glutamyltransferase activity in a corresponding wild type of the microorganism.

9. The method according to claim 6, wherein the microorganism is *Escherichia coli*.

10. The method according to claim 7, wherein the microorganism has been modified so that γ-glutamyltransferase activity is reduced as compared to γ-glutamyltransferase activity in a corresponding wild type of the microorganism.

11. The method according to claim 7, wherein the microorganism is *Escherichia coli*.

12. The method according to claim 1, wherein the protein has an amino acid sequence having at least 99% sequence identity to the amino acid sequence of SEQ ID NO: 6, 10, or 16, and has γ-glutamylvaline synthetase activity.

13. The method according to claim 1, wherein the protein has the amino acid sequence of SEQ ID NO: 6, 10, or 16.

14. The method according to claim 1, wherein an amount of γ-Glu-Val-Gly produced in the contacting is greater than an amount of γ-Glu-Gly-Gly produced in the contacting.

15. The method according to claim 1, wherein a total amount of γ-Glu-Val and γ-Glu-Val-Gly produced in the contacting is greater than a total amount of γ-Glu-Gly and γ-Glu-Gly-Gly produced in the contacting.

16. The method according to claim 1, wherein the glutathione synthetase is a protein encoded by the gshB gene of *Escherichia coli* or the GSH2 gene of *Saccharomyces cerevisiae*.

17. The method according to claim 13, wherein the glutathione synthetase is a protein encoded by the gshB gene of *Escherichia coli* or the GSH2 gene of *Saccharomyces cerevisiae*.

18. The method according to claim 1, wherein the glutathione synthetase has the amino acid sequence of SEQ ID NO: 28.

19. The method according to claim 13, wherein the glutathione synthetase has the amino acid sequence of SEQ ID NO: 28.

* * * * *